(12) United States Patent
Breyta et al.

(10) Patent No.: US 7,297,811 B2
(45) Date of Patent: Nov. 20, 2007

(54) PRECURSORS TO FLUOROALKANOL-CONTAINING OLEFIN MONOMERS AND ASSOCIATED METHODS OF SYNTHESIS AND USE

(75) Inventors: Gregory Breyta, San Jose, CA (US); Richard Anthony DiPietro, Campbell, CA (US); Daniel Joseph Dawson, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 582 days.

(21) Appl. No.: 10/729,453

(22) Filed: Dec. 4, 2003

(65) Prior Publication Data
US 2005/0124827 A1 Jun. 9, 2005

(51) Int. Cl.
*C07C 69/13* (2006.01)
*C07C 69/62* (2006.01)
*C07C 69/65* (2006.01)
*C07C 69/003* (2006.01)

(52) U.S. Cl. ............... 560/223; 560/205; 560/219; 560/220; 560/206; 560/207

(58) Field of Classification Search ........... 560/205, 560/219, 220, 223, 206, 207
See application file for complete search history.

(56) References Cited

U.S. PATENT DOCUMENTS 3,444,148 A  5/1969  Adelman

FOREIGN PATENT DOCUMENTS

| WO | WO 01/86352 | 11/2001 |
|---|---|---|
| WO | WO 02/079287 | 10/2002 |
| WO | WO 03/040827 | 5/2003 |

OTHER PUBLICATIONS

Bae et al. (2003), "Rejuvenation of 248 nm Resist Backbones for 157 nm Lithogrpahy," *Journal of Photopolymer Science and Technology* 14(4):613-620.
Fedynshyn et al. (2001), "High Resolution Fluorocarbon Based Resist for 157-nm Lithography," *Advances in Resist Technology And Processing XVIII, Proceedings of SPIE* 4345:296-307.
Ito et al. (2001), "Polymer Design for 157 nm Chemically Amplified Resists," *Advances In Resist Technology And Processing XVIII, Proceedings of SPIE* 4345:273-284.
Kunz et al. (2001), "Experimental VUV Absorbance Study of Fluorine-Functionalized Polystyrenes," *Advances in Resist Technology and Processing XVIII, Proceedings of SPIE* 4345:285-295.
Urry et al. (1968), "Multiple Multicenter Reactions of Perfluoro Ketones with Olefins," *The Journal of Organic Chemistry* 33(6):2302-2310.

*Primary Examiner*—Elvis O. Price
(74) *Attorney, Agent, or Firm*—Dianne E. Reed; Mintz, Levin, Cohn, Ferris, Glovsky and Popeo, PC; Isaac M. Rutenberg

(57) ABSTRACT

The invention provides alkene fluoroalkanol and fluorinated polyol precursors to fluoroalkanol-substituted $\alpha,\beta$-unsaturated esters. The fluoroalkanol-substituted $\alpha,\beta$-unsaturated esters are olefins that can be readily polymerized to provide fluoroalkanol-substituted polymers useful in lithographic photoresist compositions. Also provided are methods for synthesizing the alkene fluoroalkanol and fluorinated polyol precursors.

21 Claims, No Drawings

PRECURSORS TO FLUOROALKANOL-CONTAINING OLEFIN MONOMERS AND ASSOCIATED METHODS OF SYNTHESIS AND USE

TECHNICAL FIELD

This invention relates generally to the fields of polymer chemistry, lithography, and semiconductor fabrication. More specifically, the invention relates to novel compounds useful as precursors to fluoroalkanol-containing olefin monomers that are capable of undergoing polymerization to form a polymer suitable for use in a lithographic photoresist composition, particularly in a chemical amplification photoresist composition. The invention also relates to a method for synthesizing the novel precursors from a substituted olefinic reactant and a fluorinated carbonyl compound, to a method for using the precursors in the synthesis of fluoroalkanol-containing olefin monomers, and to related methods and compositions.

BACKGROUND OF THE INVENTION

The patterning of radiation-sensitive polymeric films with high energy radiation such as photons, electrons or ion beams is the principal means of defining high resolution circuitry found in semiconductor devices. The radiation-sensitive films, often referred to as "photoresists" regardless of the radiation source, generally consist of multicomponent formulations that are usually spin-cast onto a desired substrate such as a silicon wafer. The radiation is most commonly ultraviolet light of the wavelengths of 436, 365, 257, 248, 193 or 157 nanometers (nm), or a beam of electrons or ions, or "soft" x-ray radiation, also referred to as "extreme ultraviolet" (EUV) or x-rays. The radiation is exposed patternwise and induces a chemical transformation to occur that renders the solubility of the exposed regions of the films different from that of the unexposed areas when the films are treated with an appropriate developer, usually a dilute, basic aqueous solution, such as aqueous tetramethylammonium hydroxide (TMAH).

Photoresists are generally comprised of a polymeric matrix, a radiation-sensitive component, a casting solvent, and other performance enhancing additives. The highest performing photoresists in terms of sensitivity to radiation and resolution capability are the group of photoresists termed "chemically amplified." Chemically amplified photoresists allow for high resolution, high contrast, and high sensitivity that are not afforded in other photoresists. These photoresists are based on a catalytic mechanism that allows a relatively large number of chemical events such as, for example, deprotection reactions in the case of positive photoresists or crosslinking reactions in the case of negative tone photoresists, to be brought about by the application of a relatively low dose of radiation that induces formation of the catalyst, often a strong acid. The nature of the functional groups that comprise the polymeric matrix of these photoresists dictates the tone of the photoresist (positive or negative) as well as the ultimate performance attributes.

The nature of the polymeric matrix also dictates the suitability of a given photoresist for exposure with particular radiation sources. That is, the absorbance characteristics of a polymer must be carefully considered when designing a material for lithographic applications. This is important with optical lithography where polymers are chosen to provide a relatively transparent matrix for radiation-sensitive compounds such as photoacid generators (PAGs). Absorbance characteristics are also important because the wavelength of radiation used in optical lithography is directly proportional to the ultimate resolution attainable with a photoresist. The desire for higher resolution causes a continuing drive to shorter and shorter radiation wavelengths. For example, the phenolic polymers used for 248 nm imaging, namely derivatives of poly(4-hydroxystyrene)(PHS), are unsuitable for use with 193 nm radiation as the opacity of these PHS materials at 193 nm does not allow for sufficient radiation to create an appropriate image profile throughout the photoresist film thickness. That is, in order for photoresists to function properly, their films must be transparent enough at the exposing wavelength to enable sufficient light to penetrate to the bottom of the film to create usable developed relief images.

In addition to exhibiting the requisite transparency at a particular wavelength, it is important that a photoresist polymer be sufficiently polar so as to ensure solubility in industry standard developers. Polymers having lower solubility in these developers reduce the efficiency of resist development, a significant drawback in the manufacturing process.

There is, accordingly, a need in the art for a cost-effective and controllable method for incorporating functionality into polymers to impart desirable properties, including both polarity (and thus solubility in aqueous acid or base) and transparency at a particular wavelength. U.S. Pat. No. 3,444,148 to Adelman describes polymers prepared by direct polymerization of an alkene hexafluoroalcohol (i.e., an alkene containing a —$C(CF_3)_2$—OH group) with a variety of comonomers. The resulting copolymer compositions were found to have desirable characteristics relative to homopolymers that did not have an incorporated hexafluoroalcohol (HFA) group. This approach suffers from low incorporation of the desired HFA functionality (less than 2 mole percent) and is wasteful of valuable fluorinated monomer.

Incorporation of fluorinated alcohols into polymers for use in photoresist compositions has recently been described, but the availability of the requisite materials is limited. An attempt to incorporate an HFA moiety into polymerizable ethylene-containing monomers (vinyl ethers and some olefins) has been described in International Patent Publication Nos. WO 02/079287 A1, WO 01/86352 A2 and WO 03/040827 (DuPont). The methodology described in the aforementioned references involves the reaction of a heteroatom nucleophile with hexafluoroisobutene oxide. This restrictive chemistry limits the structural diversity of target molecules and is not suitable for the preparation of acrylate or methacrylate monomers.

Accordingly, there is an ongoing need for new compounds and methods that can be used to "tailor" the properties of a photoresist composition. Optimally, such compounds and methods would enable preparation of a broad range of polymer structures having desirable properties without need for costly starting materials or complex syntheses. The present invention is directed to the aforementioned need in the art, and, in part, provides compounds and methods that allow for the incorporation of fluoroalkylalcohol (i.e., fluorinated hydroxyalkyl or "fluoroalkanol") groups in a cost-effective, controlled, reproducible manner.

SUMMARY OF THE INVENTION

In a first embodiment, a method is provided for synthesizing an alkene fluoroalkanol, i.e., an alkene containing a semi-fluorinated or perfluorinated hydroxyalkyl group. These alkene fluoroalkanols, which are new compositions of matter, are particularly useful as starting materials in the preparation of polymerizable olefin monomers via saturated fluorinated polyol intermediates. The alkene fluoroalkanols have the structure of formula (III)

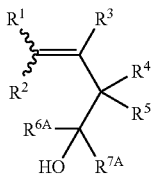

(III)

wherein:

$R^1$ is selected from hydrogen, $C_1$-$C_{24}$ alkyl, substituted $C_1$-$C_{24}$ alkyl, $C_1$-$C_{24}$ alkoxy, and substituted $C_1$-$C_{24}$ alkoxy;

$R^2$ is selected from hydrogen, $C_1$-$C_{24}$ alkyl and substituted $C_1$-$C_{24}$ alkyl;

$R^3$, $R^4$, and $R^5$ are independently selected from hydrogen, $C_1$-$C_{24}$ alkyl, and substituted $C_1$-$C_{24}$ alkyl, and further wherein any two of $R^1$, $R^2$, $R^3$, $R^4$, and $R^5$ may be taken together to form a ring;

$R^{6A}$ is selected from hydrogen, $C_1$-$C_{24}$ alkyl, substituted $C_1$-$C_{24}$ alkyl, and —(CO)—R in which R is hydrogen, hydroxyl, halo, $C_1$-$C_{24}$ alkyl, substituted $C_1$-$C_{24}$ alkyl, amino, $C_1$-$C_{24}$ alkylamino, or di($C_1$-$C_{24}$ alkyl)amino; and $R^{7A}$ is $C_1$-$C_{24}$ alkyl or substituted $C_1$-$C_{24}$ alkyl, and further wherein $R^{6A}$ and $R^{7A}$ may be taken together to form a ring, with the proviso that at least one of $R^{6A}$ and $R^{7A}$ is fluorinated. As indicated, $R^1$ and $R^2$ can be in either the (E) or (Z) configuration.

The method for synthesizing the alkene fluoroalkanols of the invention involves contacting (a) an olefinic reactant directly substituted on an olefinic carbon atom with a substituted or unsubstituted methyl group with (b) a fluorinated carbonyl-containing compound, e.g., a fluorinated ketone, under conditions and for a time period effective to allow addition of the olefinic reactant to the carbonyl carbon of the fluorinated ketone.

In another embodiment, the invention pertains to fluorinated polyols that may be synthesized in a straightforward, one-step hydroboration reaction from the aforementioned alkene fluoroalkanols. The reaction involves hydroxylating the alkene functionality in the alkene fluoroalkanol, giving rise to a a fluorinated polyol in the form of a saturated fluoroalkanol containing at least one additional hydroxyl group relative to the alkene fluoroalkanol precursor. Representative fluorinated polyols of the invention have the structure of formula (IV)

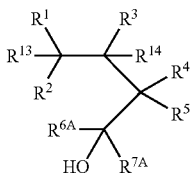

(IV)

wherein $R^1$ is selected from hydrogen, $C_1$-$C_{24}$ alkyl, substituted $C_1$-$C_{24}$ alkyl, $C_1$-$C_{24}$ alkoxy, and substituted $C_1$-$C_{24}$ alkoxy;

$R^2$, $R^3$, $R^4$, and $R^5$ are independently selected from hydrogen, $C_1$-$C_{24}$ alkyl, and substituted $C_1$-$C_{24}$ alkyl, and further wherein any two of $R^1$, $R^2$, $R^3$, $R^4$, and $R^5$ may be taken together to form a ring;

$R^{6A}$ is selected from hydrogen, $C_1$-$C_{24}$ alkyl, substituted $C_1$-$C_{24}$ alkyl, and —(CO)—R in which R is hydrogen, hydroxyl, halo, $C_1$-$C_{24}$ alkyl, substituted $C_1$-$C_{24}$ alkyl, amino, $C_1$-$C_{24}$ alkylamino, or di($C_1$-$C_{24}$ alkyl)amino;

$R^{7A}$ is $C_1$-$C_{24}$ alkyl or substituted $C_1$-$C_{24}$ alkyl, and further wherein $R^{6A}$ and $R^{7A}$ may be taken together to form a ring, with the proviso that at least one of $R^{6A}$ and $R^{7A}$ is fluorinated; and one of $R^{13}$ and $R^{14}$ is hydroxyl and the other is selected from hydrogen and hydroxyl.

In a further embodiment of the invention, a fluorinated polyol as just described is esterified with an acylation reagent such as an acyl chloride, an anhydride, or a carboxylic acid to provide a fluoroalkanol-substituted α,β-unsaturated ester such as that having the structure of formula (V)

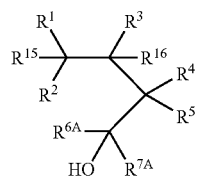

(V)

wherein $R^1$ is selected from hydrogen, $C_1$-$C_{24}$ alkyl, substituted $C_1$-$C_{24}$ alkyl, $C_1$-$C_{24}$ alkoxy, and substituted $C_1$-$C_{24}$ alkoxy;

$R^2$, $R^3$, $R^4$, and $R^5$ are independently selected from hydrogen, $C_1$-$C_{24}$ alkyl, and substituted $C_1$-$C_{24}$ alkyl, and further wherein any two of $R^1$, $R^2$, $R^3$, $R^4$, and $R^5$ may be taken together to form a ring;

$R^{6A}$ is selected from hydrogen, $C_1$-$C_{24}$ alkyl, substituted $C_1$-$C_{24}$ alkyl, and —(CO)—R in which R is hydrogen, hydroxyl, halo, $C_1$-$C_{24}$ alkyl, substituted $C_1$-$C_{24}$ alkyl, amino, $C_1$-$C_{24}$ alkylamino, or di($C_1$-$C_{24}$ alkyl)amino;

$R^{7A}$ is $C_1$-$C_{24}$ alkyl or substituted $C_1$-$C_{24}$ alkyl, and further wherein $R^{6A}$ and $R^{7A}$ may be taken together to form a ring, with the proviso that at least one of $R^{6A}$ and $R^{7A}$ is fluorinated; and one of $R^{15}$ and $R^{16}$ is hydrogen, and the other has the structure of formula (VI)

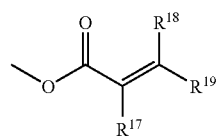

(VI)

in which $R^{17}$ is selected from hydrogen, fluoro, $C_1$-$C_4$ alkyl, fluorinated $C_1$-$C_4$ alkyl, —$CH_2$—COOH, —$CF_2$—COOH, —$CH_2$—$COOR^{20}$, and —$CF_2$—$COOR^{20}$, $R^{18}$ is hydrogen or fluoro, $R^{19}$ is hydrogen, fluoro, or —COOH, and $R^{20}$ is a nonhydrogen substituent.

The invention also provides a general method for synthesizing a fluoroalkanol-substituted α,β-unsaturated ester which accommodates a variety of reactants and substitutions, the method comprising:

(a) contacting (i) an olefinic reactant directly substituted on an olefinic carbon atom with a substituted or unsubstituted methyl group with (ii) a fluorinated carbonyl compound under reaction conditions and for a time period effective to allow addition of the olefinic reactant to the carbonyl carbon of the fluorinated carbonyl compound, thereby providing an alkene fluoroalkanol;

(b) hydroxylating the alkene functionality in the alkene fluoroalkanol by subjecting the alkene fluoroalkanol to a hydroboration reaction, thereby providing a saturated fluoroalkanol containing at least one additional hydroxyl group;

(c) acylating the additional hydroxyl group by contacting the saturated fluoroalkanol with an acylation reagent selected from acyl chlorides and anhydrides under esterification conditions.

The fluoroalkanol-substituted esters so provided are polymerizable olefins that can be used to prepare polymers and copolymers having transparency at a desired wavelength, e.g., 248 nm, 193 nm, 157 nm, or 13.4 nm, such that the polymers and copolymers can be advantageously employed in a lithographic photoresist composition.

DETAILED DESCRIPTION OF THE INVENTION

I. Definitions and Nomenclature

Unless otherwise indicated, this invention is not limited to specific compositions, components, or process steps. It should also be noted that the singular forms "a" and "the" are intended to encompass plural referents, unless the context clearly dictates otherwise. The terminology used herein is for the purpose of describing particular embodiments only and is not intended to be limiting.

In this specification and in the claims that follow, reference will be made to a number of terms, which shall be defined to have the following meanings:

As used herein, the phrase. "having the formula" or "having the structure" is not intended to be limiting and is used in the same way that the term "comprising" is commonly used.

The term "alkyl" as used herein refers to a linear or branched, saturated hydrocarbon substituent that generally, although not necessarily, contains 1 to about 24 carbon atoms, such as methyl, ethyl, n-propyl, isopropyl, n-butyl, isobutyl, t-butyl, octyl, decyl, tetradecyl, hexadecyl, eicosyl, tetracosyl, and the like. Generally, although again not necessarily, alkyl groups herein contain 1 to about 12 carbon atoms, more typically 1 to about 8 carbon atoms. The term "lower alkyl" intends an alkyl group of 1 to 6 carbon atoms, and the term "cycloalkyl" intends a cyclic alkyl group, typically having 3 to 8, preferably 3 to 7, carbon atoms. The term "substituted alkyl" refers to alkyl substituted with one or more substituent groups, i.e., wherein a hydrogen atom is replaced with a non-hydrogen substituent group, and the terms "heteroatom-containing alkyl" and "heteroalkyl" refer to alkyl substituents in which at least one carbon atom is replaced with a heteroatom such as O, N, or S. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear or branched saturated hydrocarbon linkage, typically although not necessarily containing 1 to about 24 carbon atoms, such as methylene, ethylene, n-propylene, n-butylene, n-hexylene, decylene, tetradecylene, hexadecylene, and the like. Preferred alkylene linkages contain 1 to about 12 carbon atoms, more preferred alkylene linkages contain 1 to about 8 carbon atoms, and the term "lower alkylene" refers to an alkylene linkage of 1 to 6 carbon atoms, preferably 1 to 4 carbon atoms. The term "substituted alkylene" refers to an alkylene linkage substituted with one or more substituent groups, i.e., wherein a hydrogen atom is replaced with a non-hydrogen substituent group, and the terms "heteroatom-containing alkylene" and "heteroalkylene" refer to alkylene linkages in which at least one carbon atom is replaced with a heteroatom. If not otherwise indicated, the terms "alkylene" and "lower alkylene" include linear, branched, cyclic, unsubstituted, substituted, and/or heteroatom-containing alkylene and lower alkylene, respectively.

The term "alicyclic" is used to refer to cyclic, non-aromatic compounds, substituents and linkages, e.g., cycloalkanes and cycloalkenes, cycloalkyl and cycloalkenyl substituents, and cycloalkylene and cycloalkenylene linkages. Often, the term refers to polycyclic compounds, substituents, and linkages, including bridged bicyclic, compounds, substituents, and linkages. Preferred alicyclic moieties herein contain in the range of 3 to about 30 carbon atoms, typically 3 to about 18 carbon atoms, and more typically 5 to about 14 carbon atoms. Unless otherwise indicated, the term "alicyclic" includes substituted and/or heteroatom-containing such moieties. It will be appreciated that the term "cyclic," as used herein, thus includes "alicyclic" moieties.

The term "fluorinated" refers to replacement of a hydrogen atom in a molecule or molecular segment with a fluorine atom, and includes perfluorinated moieties. The term "perfluorinated" is also used in its conventional sense to refer to a molecule or molecular segment wherein all hydrogen atoms are replaced with fluorine atoms, while the term "semi-fluorinated" refers to a molecule or molecular segment wherein fewer than all hydrogen atoms are replaced with fluorine atoms. Thus, a "fluorinated" methyl group encompasses —$CH_2F$ and —$CHF_2$ as well as the "perfluorinated" methyl group, i.e., —$CF_3$ (trifluoromethyl).

The term "fluoroalkanol" as used herein refers to a compound or substituent containing a fluorinated, hydroxyl-substituted alkyl group, with "alkyl" defined as above. Fluoroalkanols and fluoroalcohol substituents may be semi-fluorinated or perfluorinated.

The term "heteroatom-containing" as in a "heteroatom-containing alkyl group" (also termed a "heteroalkyl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Examples of heteroalkyl groups include alkoxyalkyl, alkoxyaryl, alkylthio-substituted alkyl, and the like.

Unless otherwise indicated, the term "hydrocarbyl" is to be interpreted as including substituted and/or heteroatom-containing hydrocarbyl moieties. "hydrocarbyl" refers to univalent hydrocarbyl radicals containing 1 to about 30 carbon atoms, preferably 1 to about 18 carbon atoms, most preferably 1 to about 12 carbon atoms, including linear, branched, cyclic, alicyclic, and aromatic species. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

The term "polyol" refers to an organic compound containing two or more hydroxyl groups.

By "substituted" as in "substituted alkyl," "substituted alkylene," and the like, as alluded to in some of the aforementioned definitions, it is meant that in the alkyl, alkylene, or other moiety, at least one hydrogen atom bound to a carbon (or other) atom is replaced with a non-hydrogen substituent. Examples of such substituents include, without limitation, functional groups such as halide, hydroxyl, sulfhydryl, alkoxy, and acyl (including alkylcarbonyl (—CO-alkyl)), and hydrocarbyl moieties such as alkyl, including linear, branched, and cyclic alkyl. The functional groups may, if a particular group permits, be further substituted with one or more additional functional groups or with one or more hydrocarbyl moieties such as those specifically enumerated, and analogously, a hydrocarbyl substituent may be further substituted with one or more functional groups or additional hydrocarbyl moieties such as those specifically enumerated.

When two substituents are indicated as being "taken together to form a ring," several possibilities are encompassed. That is, when R and R' of the following hypothetical compound are indicated as being taken together to form a ring

the resulting compounds include (1) those wherein a single spacer atom links the carbon atoms indicated at * and ** (i.e., R and R' "taken together" together form a single atom that may or may not be substituted, e.g., $CH_2$ or O), (2) those wherein a direct covalent bond is formed between R and R', and (3) those wherein R and R' are linked through a bifunctional moiety containing one or more spacer atoms. In addition, compounds in which R and R' are "taken together to form a ring" include compounds in which the linked atoms are not necessarily contained within a terminal group. For example, when R of the above formula is —$CH_2CH_3$ and R' is —$CH_2CF_3$, such that the compound has the structure

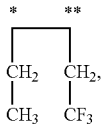

then compounds in which R and R' are taken together to form a ring include both

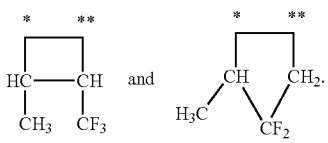

The term "ring" is intended to include all types of cyclic groups, although the rings of primary interest herein are alicyclic, including cycloalkyl and substituted and/or heteroatom-containing cycloalkyl, whether monocyclic, bicyclic (including bridged bicyclic), or polycyclic. Preferred rings are substituted and/or heteroatom-containing monocyclic rings.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

II. Alkene Fluoroalkanols and Synthesis thereof

In one aspect of the invention, novel alkene fluoroalkanols are provided, as is a method is provided for synthesizing an alkene fluoroalkanol. The alkene fluoroalkanols of the invention, which are alkenes containing a fluorinated hydroxyalkyl group, are particularly useful as starting materials in the synthesis of polymerizable olefin monomers via unsaturated fluoroalkanol intermediates. The alkene fluoroalkanols have the structure of formula (III)

wherein the substituents indicated are as follows:

$R^1$ is selected from hydrogen, $C_1$-$C_{24}$ alkyl, substituted $C_1$-$C_{24}$ alkyl (e.g., fluorinated $C_1$-$C_{24}$ alkyl), $C_1$-$C_{24}$ alkoxy, and substituted $C_1$-$C_{24}$ alkoxy (e.g., fluorinated $C_1$-$C_{24}$ alkoxy). Preferred $R^1$ moieties include, without limitation, hydrogen, $C_1$-$C_{12}$ alkyl, $C_1$-$C_{12}$ hydroxyalkyl, fluorinated $C_1$-$C_{12}$ alkyl, fluorinated $C_3$-$C_{12}$ hydroxyalkyl, fluorinated $C_3$-$C_{12}$ alkyl substituted with a protected hydroxyl group, and $C_1$-$C_{12}$ alkoxy, while more preferred $R^1$ moieties are hydrogen, $C_1$-$C_8$ alkyl, $C_1$-$C_8$ alkoxy, and fluorinated hydroxyalkyl having the structure -$(L^1)_{n1}$—$CR^8R^9$—OH in which n1 is zero or 1, $L^1$ is $C_1$-$C_6$ aliphatic, $R^8$ is selected from hydrogen, $C_1$-$C_8$ alkyl, and fluorinated $C_1$-$C_8$ alkyl, and $R^9$ is fluorinated $C_1$-$C_8$ alkyl. Optimally, $R^1$ is selected from hydrogen, $C_1$-$C_4$ alkyl, $C_1$-$C_4$ alkoxy, and -$(L^1)_{n1}$—$CR^8R^9$—OH in which n1 is zero or 1, $L^1$ is $C_1$-$C_4$ aliphatic, $R^8$ is selected from hydrogen, methyl, trifluoromethyl, difluoromethyl, and fluoromethyl, and $R^9$ is selected from methyl, trifluoromethyl, difluoromethyl, and fluoromethyl. For example, $R^1$ may be methyl, ethyl, n-propyl, isopropyl, n-butyl, s-butyl, methoxy, ethoxy, 2-methoxy-propyl, —CH($CF_3$)—OH, —C($CH_3$)($CF_3$)—OH, —C($CF_3$)($CF_3$)—OH, —CH($CHF_2$)—OH, —C($CH_3$)($CHF_2$)—OH, —C($CF_3$)($CHF_2$)—OH, —CH($CH_2F$)—OH, —C($CH_3$)($CH_2F$)—OH, —C($CF_3$)($CH_2F$)—OH, —C($CF_2H$)($CH_2F$)—OH, —$CH_2$—CH($CF_3$)—OH, —$CH_2$—C($CH_3$)($CF_3$)—OH, —$CH_2$—C($CF_3$)$_2$—OH, —$CH_2$—CH($CHF_2$)—OH, —$CH_2$—C($CH_3$)($CHF_2$)—OH, —$CH_2$—C($CHF_2$)$_2$—OH, —$CH_2$—CH($CH_2F$)—OH, —$CH_2$—C($CH_3$)($CH_2F$)—OH, —$CH_2$—C($CH_2F$)$_2$—OH, —$CF_2$—CH($CF_3$)—OH, —$CF_2$—C($CH_3$)($CF_3$)—OH, —$CF_2$—C($CF_3$)$_2$—OH, —$CF_2$—CH($CHF_2$)—OH, —$CF_2$—C($CH_3$)($CHF_2$)—OH, —CF$_2$—C(CHF$_2$)$_2$—OH, —CF$_2$—CH(CH$_2$F)—OH, —CF$_2$—C(CH$_3$)(CH$_2$F)—OH, or —CF$_2$—C(CH$_2$F)$_2$—OH.

R$^2$ is selected from hydrogen, C$_1$-C$_{24}$ alkyl and substituted C$_1$-C$_{24}$ alkyl (e.g., fluorinated C$_1$-C$_{24}$ alkyl), and is preferably hydrogen, C$_1$-C$_{12}$ alkyl, or substituted C$_1$-C$_{12}$ alkyl, particularly fluorinated C$_1$-C$_{12}$ alkyl. More preferably, R$^2$ is hydrogen or C$_1$-C$_8$ alkyl, and, most preferably, R$^2$ is hydrogen or C$_1$-C$_4$ alkyl, e.g., methyl, ethyl, n-propyl, isopropyl, n-butyl, or the like.

R$^3$, R$^4$, and R$^5$ are independently selected from hydrogen, C$_1$-C$_{24}$ alkyl, and substituted C$_1$-C$_{24}$ alkyl, and are preferably selected from C$_1$-C$_{12}$ alkyl, C$_1$-C$_{12}$ hydroxyalkyl, fluorinated C$_1$-C$_{12}$ alkyl, fluorinated C$_1$-C$_{12}$ hydroxyalkyl, and fluorinated C$_1$-C$_{12}$ alkyl substituted with a protected hydroxyl group. Typically, R$^3$, R$^4$, and R$^5$ are selected from hydrogen, C$_1$-C$_8$ alkyl, and fluorinated hydroxyalkyl having the structure -(L$^2$)$_{n2}$—CR$^{8A}$R$^{9A}$—OH in which: n2 is zero or 1; L$^2$ is C$_1$-C$_6$ aliphatic, preferably C$_1$-C$_4$ aliphatic; R$^{8A}$ is selected from hydrogen, C$_1$-C$_8$ alkyl, and fluorinated C$_1$-C$_8$ alkyl; and R$^{9A}$ is fluorinated C$_1$-C$_8$ alkyl. For example, R$^{8A}$ may be hydrogen, methyl, trifluoromethyl, difluoromethyl, or fluoromethyl, and R$^{9A}$ may be methyl, trifluoromethyl, difluoromethyl, or fluoromethyl.

It should also be noted that any two of R$^1$, R$^2$, R$^3$, R$^4$, and R$^5$ may be taken together to form a ring, generally a C$_3$-C$_{30}$ alicyclic group, preferably a C$_3$-C$_{18}$ alicyclic group, and typically a C$_5$-C$_{14}$ alicyclic group. Such alicyclic groups include substituted alicyclic groups, particularly fluorinated alicyclic groups. Examples of alicyclic groups that may be formed by two of R$^1$, R$^2$, R$^3$, R$^4$, and R$^5$ include, without limitation, cyclopentyl, cyclohexyl, adamantyl, norbornyl, and substituted analogs thereof.

R$^{6A}$ and R$^{7A}$ are substituents within the fluoroalkanol group —CR$^{6A}$R$^{7A}$—OH, and, accordingly, at least one of R$^{6A}$ and R$^{7A}$ is fluorinated. In general, R$^{6A}$ is selected from hydrogen, C$_1$-C$_{24}$ alkyl, substituted C$_1$-C$_{24}$ alkyl, and —(CO)—R in which R is hydrogen, hydroxyl, halo, C$_1$-C$_{24}$ alkyl, substituted C$_1$-C$_{24}$ alkyl (including fluorinated C$_1$-C$_{24}$ alkyl), amino, C$_1$-C$_{24}$ alkylamino, or di(C$_1$-C$_{24}$ alkyl)amino, and R$^{7A}$ is C$_1$-C$_{24}$ alkyl or substituted C$_1$-C$_{24}$ alkyl (including fluorinated C$_1$-C$_{24}$ alkyl). More typically, R$^{6A}$ is selected from hydrogen, C$_1$-C$_{12}$ alkyl, and C$_1$-C$_{12}$ haloalkyl, and R$^{7A}$ is C$_1$-C$_{12}$ alkyl or fluorinated C$_1$-C$_{12}$ alkyl. In a preferred embodiment, R$^{6A}$ is selected from hydrogen, C$_1$-C$_8$ alkyl, and fluorinated C$_1$-C$_8$ alkyl; and R$^{7A}$ is C$_1$-C$_8$ alkyl or fluorinated C$_1$-C$_8$ alkyl. Optimally, R$^{6A}$ is selected from hydrogen, C$_1$-C$_4$ alkyl, semi-fluorinated C$_1$-C$_4$ alkyl, and perfluorinated C$_1$-C$_4$ alkyl, and R$^{7A}$ is selected from C$_1$-C$_4$ alkyl, semi-fluorinated C$_1$-C$_4$ alkyl, and perfluorinated C$_1$-C$_4$ alkyl. Exemplary —CR$^{6A}$R$^{7A}$—OH groups thus include —CH(CF$_3$)—OH, —C(CH$_3$)(CF$_3$)—OH, —C(CF$_3$)(CF$_3$)—OH, —CH(CHF$_2$)—OH, —C(CH$_3$)(CHF$_2$)—OH, —C(CF$_3$)(CHF$_2$)—OH, —CH(CH$_2$F)—OH, —C(CH$_3$)(CH$_2$F)—OH, and —C(CF$_2$H)(CH$_2$F)—OH. Particularly preferred —CR$^{6A}$R$^{7A}$—OH moieties are those wherein R$^{6A}$ and R$^{7A}$ are both trifluoromethyl and those wherein one of R$^{6A}$ and R$^{7A}$ is methyl and the other is trifluoromethyl, i.e., —C(CH$_3$)(CF$_3$)—OH and —C(CF$_3$)(CF$_3$)—OH. In addition, R$^{6A}$ and R$^{7A}$ may be taken together to form a ring, e.g., a fluorinated alicyclic group, of C$_3$-C$_{30}$, preferably C$_3$-C$_{18}$, and most preferably C$_5$-C$_{14}$ carbon atoms. The alicyclic group may be unsubstituted or substituted, e.g., with one or more fluorine atoms.

Representative alkene fluoroalkanols of the invention include, but are not limited to, the following specific compounds:

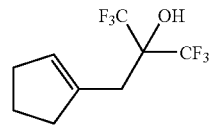

2-(Cyclopenten-1'-yl)-1,1,1-trifluoro-2-trifluoromethyl-2-propanol

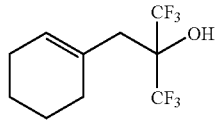

2-(Cyclohexen-1'-yl)-1,1,1-trifluoro-2-trifluoromethyl-2-propanol

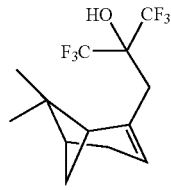

2-(6',6'-Dimethylbicyclo[3.1.1]heptene-2'-yl)-1,1,1-trifluoro-2-trifluoromethyl-2-propanol

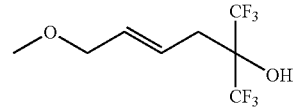

6-Methoxy-1,1,1-trifluoro-2-trifluoromethylhex-4-en-2-ol

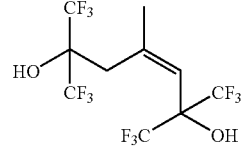

1,1,1,7,7,7,-Hexafluoro-2,6-bis(trifluoromethyl)-4-methyl-2,6-hept-3-ene-2,6-diol

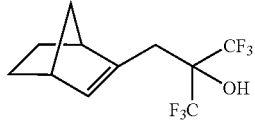

3-Bicyclo[2.2.1]hept-2-ene-2-yl)-1,1,1-trifluoro-2-trifluoromethyl-2-propanol

The alkene fluoroalkanols of the invention are synthesized in a straightforward, single step reaction. The reaction involves contacting an olefinic reactant directly substituted on an olefinic carbon atom with a substituted or unsubstituted methyl group with a fluorinated carbonyl compound under reaction conditions and for a time period effective to allow addition of the olefinic reactant to the carbonyl carbon of the fluorinated carbonyl compound. The fluorinated carbonyl compound may be symmetrically or asymmetrically substituted, and in one embodiment excludes hexafluoroacetone. The reaction is illustrated in Scheme 1:

Scheme 1

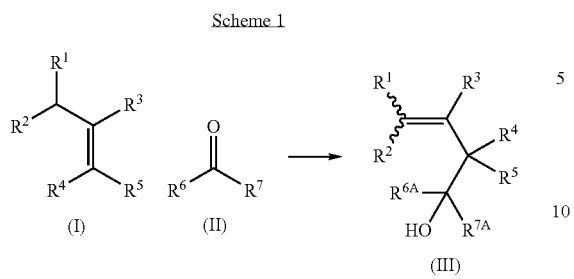

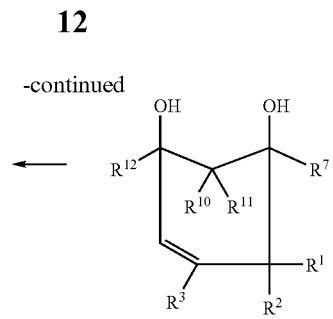

In reactant (I), $R^1$, $R^2$, $R^3$, $R^4$, and $R^5$ are as defined previously, and it will be appreciated that the substituted or unsubstituted methyl group is the —$CR^1R^2$ moiety shown within the structure. In reactant (II), $R^6$ is selected from hydrogen, $C_1$-$C_{24}$ alkyl, substituted $C_1$-$C_{24}$ alkyl (e.g., fluorinated $C_1$-$C_{24}$ alkyl), $C_3$-$C_{25}$ acylmethyl, (fluorinated $C_2$-$C_{24}$ acyl)-substituted methyl, (fluorinated $C_2$-$C_{24}$ acyl)-substituted difluoromethyl, and —(CO)—R in which R is hydrogen, hydroxyl, halo, $C_1$-$C_{24}$ alkyl, substituted $C_1$-$C_{24}$ alkyl, amino, $C_1$-$C_{24}$ alkylamino, or di($C_1$-$C_{24}$ alkyl)amino, and $R^7$ is $C_1$-$C_{24}$ alkyl or fluorinated $C_1$-$C_{24}$ alkyl, with the proviso that at least-one of $R^6$ and $R^7$ is fluorinated. However, $R^6$ is generally selected from hydrogen, $C_1$-$C_{12}$ alkyl, $C_1$-$C_{12}$ haloalkyl, $C_3$-$C_{13}$ acylmethyl, (fluorinated $C_2$-$C_{12}$ acyl)-substituted methyl, and (fluorinated $C_2$-$C_{12}$ acyl)-substituted difluoromethyl, while $R^7$ is generally $C_1$-$C_{12}$ alkyl or fluorinated $C_1$-$C_{12}$ alkyl. Preferably, $R^6$ is selected from hydrogen, $C_1$-$C_8$ alkyl, fluorinated $C_1$-$C_8$ alkyl, $C_3$-$C_9$ acylmethyl, (fluorinated $C_2$-$C_8$ acyl)-substituted methyl, and (fluorinated $C_2$-$C_8$ acyl)-substituted difluoromethyl, and $R^7$ is $C_1$-$C_8$ alkyl or fluorinated $C_1$-$C_8$ alkyl. Optimally, $R^6$ is selected from hydrogen, $C_1$-$C_4$ alkyl, semi-fluorinated $C_1$-$C_4$ alkyl, perfluorinated $C_1$-$C_4$ alkyl, and $R^{12}$—(CO)—$CR^{10}R^{11}$— in which $R^{10}$ and $R^{11}$ are H or F and $R^{12}$ is methyl or trifluoromethyl, and $R^7$ is selected from $C_1$-$C_4$ alkyl, semi-fluorinated $C_1$-$C_4$ alkyl, and perfluorinated $C_1$-$C_4$ alkyl. In the product (III), $R^1$, $R^2$, $R^3$, $R^4$, $R^5$, $R^{6A}$, and $R^{7A}$ are as defined previously.

With certain fluorinated carbonyl compounds of formula (II), i.e., those containing a $R^{12}$—(CO)—$CR^{10}R^{11}$— substituent at $R^6$, cyclic alkene fluoroalkanols result as shown in Scheme 2 (for simplicity, $R^4$ and $R^5$ of the olefinic reactant (I) are H and therefore not shown):

Scheme 2

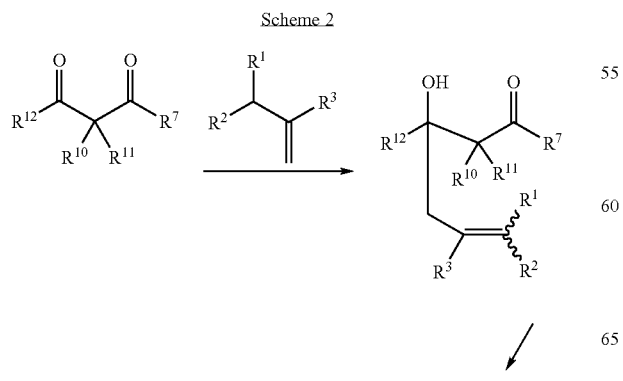

As indicated in the scheme, the cyclic alkene fluoroalkanols can then be converted to cyclic polyols, as will be described infra.

In addition, alkene fluoroalkanols substituted with two or more fluoroalkanol groups can be synthesized by using an excess of the fluorinated carbonyl reagent (II), such that two or more fluoroalkanol groups become incorporated into the compound. Such a reaction is illustrated in Scheme 3:

Scheme 3

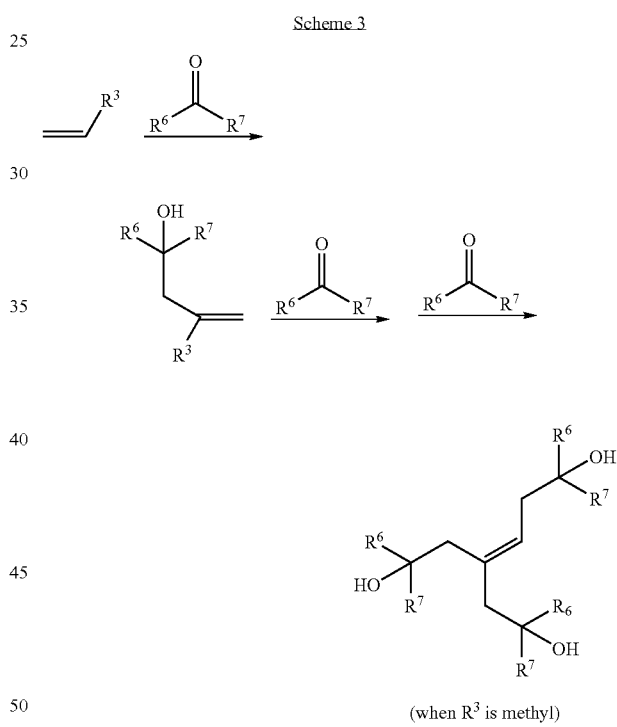

(when $R^3$ is methyl)

The reactions illustrated in Schemes 1, 2, and 3 are carried out at a temperature typically in the range of about −20° C. to about 20° C. After 2-12 hours, the temperature is raised, and the product may thereafter be isolated and optionally purified using any suitable means. A specific synthesis of an alkene fluoroalkanol is described in Example 1.

III. Fluorinated Polyols Synthesized from the Alkene Fluoroalkanols

The alkene fluoroalkanols of formula (III) are useful as precursors to saturated fluorinated polyols which, in turn, can be converted to polymerizable olefins as will be described infra. In one embodiment, the fluorinated polyols have the structure of formula (IV)

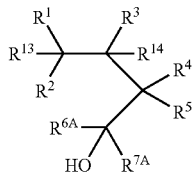

(IV)

wherein $R^1$, $R^2$, $R^3$, $R^4$, $R^5$, $R^{6A}$, and $R^{7A}$ are as defined previously for the alkene fluoroalkanols of formula (III), and one of $R^{13}$ and $R^{14}$ is hydroxyl and the other is selected from hydrogen and hydroxyl, and is usually hydrogen.

In a preferred fluorinated polyol of formula (IV):

$R^1$ is selected from hydrogen, $C_1$-$C_4$ alkyl, $C_1$-$C_4$ alkoxy, and -$(L^1)_{n1}$-$CR^8R^9$—OH in which n1 is zero or 1, $L^1$ is $C_1$-$C_4$ aliphatic, $R^8$ is selected from hydrogen, methyl, trifluoromethyl, difluoromethyl, and fluoromethyl, and $R^9$ is selected from methyl, trifluoromethyl, difluoromethyl, and fluoromethyl;

$R^2$ is hydrogen or $C_1$-$C_4$ alkyl;

$R^3$, $R^4$, and $R^5$ are independently selected from hydrogen, $C_1$-$C_4$ alkyl, and -$(L^2)_{n2}$-$CR^{8A}R^{9A}$—OH in which n2 is zero or 1, $L^2$ is $C_1$-$C_4$ aliphatic, $R^{8A}$ is selected from hydrogen, methyl, trifluoromethyl, difluoromethyl, and fluoromethyl, and $R^{9A}$ is selected from methyl, trifluoromethyl, difluoromethyl, and fluoromethyl, and further wherein any two of $R^1$, $R^3$, $R^4$, and $R^5$ may be taken together to form a $C_5$-$C_{14}$ alicyclic group;

$R^{6A}$ is selected from hydrogen, $C_1$-$C_4$ alkyl, semi-fluorinated $C_1$-$C_4$ alkyl, and perfluorinated $C_1$-$C_4$ alkyl, and is optimally methyl or trifluoromethyl; and $R^{7A}$ is selected from $C_1$-$C_4$ alkyl, semi-fluorinated $C_1$-$C_4$ alkyl, and perfluorinated $C_1$-$C_4$ alkyl, and is optimally trifluoromethyl.

In the most preferred embodiment, $R^2$ and $R^3$ are taken together to form a $C_3$-$C_{30}$ alicyclic group, preferably a $C_3$-$C_{18}$ alicyclic group, most preferably a $C_5$-$C_{14}$ alicyclic group, and $R^4$ and $R^5$ are hydrogen.

Representative fluorinated polyols of the invention include, but are not limited to, the following specific compounds:

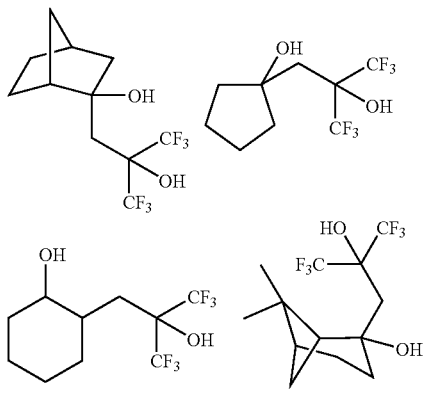

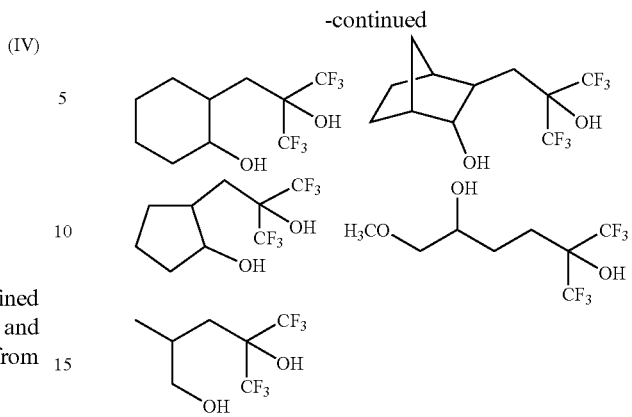

The fluorinated polyol is readily synthesized from the alkene fluoroalkanol using a hydroboration reaction, in which an alkene fluoroalkanol having the structure of formula (III) is contacted with a substituted or unsubstituted borane, followed by addition of aqueous base and hydrogen peroxide, preferably in that order, to the reaction mixture. Examples of suitable boranes are those having the structure $BHR^{54}R^{55}$ in which $R^{54}$ and $R^{55}$ are independently selected from hydrogen, halo, $C_1$-$C_{24}$ alkyl, substituted $C_1$-$C_{24}$ alkyl, $C_1$-$C_{24}$ alkoxy, substituted $C_1$-$C_{24}$ alkoxy, or wherein $R^{54}$ and $R^{55}$ may be taken together to form an alicyclic group. Preferably, $R^{54}$ and $R^{55}$ are independently selected from hydrogen, chloro, $C_1$-$C_{12}$ alkyl, substituted $C_1$-$C_{12}$ alkyl, $C_1$-$C_{12}$ alkoxy, and substituted $C_1$-$C_{12}$ alkoxy. The reaction proceeds according to Scheme 4:

Scheme 4

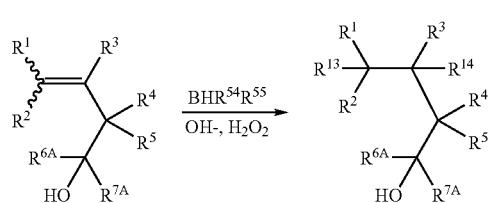

Examples 2, 3, and 9-12 describe specific reactions in which fluorinated polyols of the invention are synthesized.

IV. Fluoroalkanol-Sybstituted α,β-Unsaturated Esters

The fluorinated polyols described in part (III) of this section are readily converted to polymerizable olefins in the form of fluoroalkanol-substituted α,β-unsaturated esters, i.e., fluoralkanol-substituted acrylates, methacrylates, and analogs thereof. In one embodiment, invention provides a fluoroalkanol-substituted α,β-unsaturated ester having the structure of formula (V)

(V)

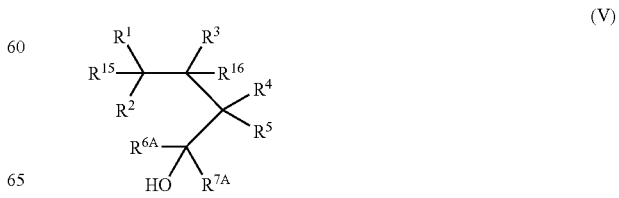

wherein:

$R^1$ is selected from hydrogen, $C_1$-$C_{24}$ alkyl, substituted $C_1$-$C_{24}$ alkyl, $C_1$-$C_{24}$ and substituted $C_1$-$C_{24}$ alkoxy;

$R^2$, $R^3$, $R^4$, and $R^5$ are independently selected from hydrogen, $C_1$-$C_{24}$ alkyl, and substituted $C_1$-$C_{24}$ alkyl, and further wherein any two of $R^1$, $R^2$, $R^3$, $R^4$, and $R^5$ may be taken together to form a ring;

$R^{6A}$ is selected from hydrogen, $C_1$-$C_{24}$ alkyl, substituted $C_1$-$C_{24}$ alkyl, and —(CO)—R in which R is hydrogen, hydroxyl, halo, $C_1$-$C_{24}$ alkyl, substituted $C_1$-$C_{24}$ alkyl, amino, $C_1$-$C_{24}$ alkylamino, or di($C_1$-$C_{24}$ alkyl)amino;

$R^{7A}$ is $C_1$-$C_{24}$ alkyl or substituted $C_1$-$C_{24}$ alkyl, and further wherein $R^{6A}$ and $R^{7A}$ may be taken together to form a ring, with the proviso that at least one of $R^{6A}$ and $R^{7A}$ is fluorinated; and one of $R^{15}$ and $R^{16}$ is hydrogen, and the other has the structure of formula (VI)

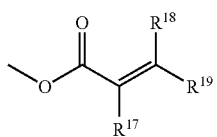

(VI)

in which $R^{17}$ is selected from hydrogen, fluoro, $C_1$-$C_4$ alkyl, fluorinated $C_1$-$C_4$ alkyl, —$CH_2$—COOH, —$CF_2$—COOH, —$CH_2$—COOR$^{20}$, and —$CF_2$—COOR$^{20}$, $R^{18}$ is hydrogen or fluoro, $R^{19}$ is hydrogen, fluoro, or —COOH, and $R^{20}$ is a nonhydrogen substituent.

In preferred compounds of formula (VI), the $R^1$, $R^2$, $R^3$, $R^4$, $R^5$, $R^{6A}$, and $R^{7A}$ substituents are defined as for preferred compounds of formulas (III) and (IV), and:

$R^{17}$ is selected from hydrogen, fluoro, methyl, trifluoromethyl, —$CH_2$—COOH, and —$CH_2$—COOR$^{20}$;

$R^{18}$ and $R^{19}$ are independently selected from hydrogen and fluoro; and $R^{20}$ is selected from $C_1$-$C_{12}$ alkyl and substituted $C_1$-$C_{12}$ alkyl.

In particularly preferred compounds of formula (V), $R^{17}$ is selected from hydrogen and methyl, and $R^{19}$ are hydrogen.

In a related embodiment, the invention provides a fluoroalkanol-substituted α,β-unsaturated ester having the structure of formula (VII)

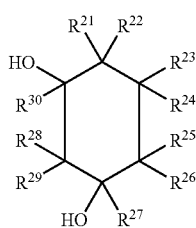

(VII)

wherein the substituents are as follows:

$R^{21}$ is selected from hydrogen, $C_1$-$C_{24}$ alkyl, substituted $C_1$-$C_{24}$ alkyl (e.g., fluorinated $C_1$-$C_{24}$ alkyl), $C_1$-$C_{24}$ alkoxy, and substituted $C_1$-$C_{24}$ alkoxy (e.g., fluorinated $C_1$-$C_{24}$ alkoxy). Preferred $R^{21}$ moieties include, without limitation, hydrogen, $C_1$-$C_{12}$ alkyl, $C_1$-$C_{12}$ hydroxyalkyl, fluorinated $C_1$-$C_{12}$ alkyl, fluorinated $C_3$-$C_{12}$ hydroxyalkyl, fluorinated $C_3$-$C_{12}$ alkyl substituted with a protected hydroxyl group, and $C_1$-$C_{12}$ alkoxy, while more preferred $R^{21}$ moieties are hydrogen, $C_1$-$C_8$ alkyl, $C_1$-$C_8$ alkoxy, and fluorinated hydroxyalkyl having the structure -($L^1$)$_{n1}$-CR$^8$R$^9$—OH in which n1, $L^1$, $R^8$, $R^9$ are as defined earlier herein. In a most preferred embodiment, $R^{21}$ is selected from hydrogen, $C_1$-$C_4$ alkyl, $C_1$-$C_4$ alkoxy, and -($L^1$)$_{n1}$-CR$^8$R$^9$—OH in which n1 is zero or 1, $L^1$ is $C_1$-$C_4$ aliphatic, $R^8$ is selected from hydrogen, methyl, trifluoromethyl, difluoromethyl, and fluoromethyl, and $R^9$ is selected from methyl, trifluoromethyl, difluoromethyl, and fluoromethyl. For example, $R^1$ may be methyl, ethyl, n-propyl, isopropyl, n-butyl, s-butyl, methoxy, ethoxy, 2-methoxy-propyl, —CH(CF$_3$)—OH, —C(CH$_3$)(CF$_3$)—OH, —C(CF$_3$)(CF$_3$)—OH, or the like.

$R^{22}$ is selected from hydrogen, $C_1$-$C_{24}$ alkyl, and substituted $C_1$-$C_{24}$ alkyl (e.g., fluorinated $C_1$-$C_{24}$ alkyl), and is preferably hydrogen, $C_1$-$C_{12}$ alkyl, or substituted $C_1$-$C_{12}$ alkyl, particularly fluorinated $C_1$-$C_{12}$ alkyl. More preferably, $R^{22}$ is hydrogen or $C_1$-$C_8$ alkyl, and, most preferably, $R^{22}$ is hydrogen or $C_1$-$C_4$ alkyl, e.g., methyl, ethyl, n-propyl, isopropyl, n-butyl, or the like.

One of $R^{23}$ and $R^{26}$ is hydrogen, and the other has the structure of formula (VI)

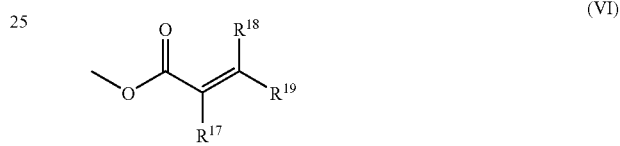

(VI)

wherein $R^{17}$, $R^{18}$, and $R^{19}$ are defined as for the fluorinated esters of formula (V). In representative compounds of formula (VII), $R^{23}$ and $R^{26}$ are both trifluoromethyl, or one of $R^{23}$ and $R^{26}$ is methyl and the other is trifluoromethyl.

$R^{24}$ and $R^{25}$ are selected from hydrogen, $C_1$-$C_{24}$ alkyl and substituted $C_1$-$C_{24}$ alkyl, or may be taken together to form a ring. Generally, $R^{24}$ and $R^{25}$ are selected from hydrogen, $C_1$-$C_{12}$ alkyl, $C_1$-$C_{12}$ hydroxyalkyl, fluorinated $C_1$-$C_{12}$ alkyl, fluorinated $C_1$-$C_{12}$ hydroxyalkyl, fluorinated $C_1$-$C_{12}$ alkyl substituted with a protected hydroxyl group, and $C_1$-$C_{12}$ alkoxy, or may be taken together to form a $C_3$-$C_{30}$ alicyclic group; preferably, $R^{24}$ and $R^{25}$ are independently selected from hydrogen, $C_1$-$C_8$ alkyl, and fluorinated hydroxyalkyl having the structure -($L^2$)$_{n2}$-CR$^{8A}$R$^{9A}$—OH in which n2, $L^2$, $R^{8A}$, and $R^{9A}$ are as defined earlier herein.

$R^{27}$ is selected from hydrogen, $C_1$-$C_{24}$ alkyl, substituted $C_1$-$C_{24}$ alkyl, and —(CO)—R in which R is hydrogen, hydroxyl, halo, $C_1$-$C_{24}$ alkyl, substituted $C_1$-$C_{24}$ alkyl, amino, $C_1$-$C_{24}$ alkylamino, or di($C_1$-$C_{24}$ alkyl)amino, and $R^{30}$ is $C_1$-$C_{24}$ alkyl or substituted $C_1$-$C_{24}$ alkyl, with the proviso that at least one of $R^{27}$ and $R^{30}$ is fluorinated. Preferably, $R^{27}$ is hydrogen, $C_1$-$C_{12}$ alkyl, and $C_1$-$C_{12}$ haloalkyl, and $R^{30}$ is $C_1$-$C_{12}$ alkyl or fluorinated $C_1$-$C_{12}$ alkyl. In a more preferred embodiment, $R^{27}$ is selected from hydrogen, $C_1$-$C_8$ alkyl, and fluorinated $C_1$-$C_8$ alkyl, and $R^{30}$ is $C_1$-$C_8$ alkyl or fluorinated $C_1$-$C_8$ alkyl. Optimally, $R^{27}$ is selected from hydrogen, $C_1$-$C_4$ alkyl, semi-fluorinated $C_1$-$C_4$ alkyl, and perfluorinated $C_1$-$C_4$ alkyl, and $R^{30}$ is selected from $C_1$-$C_4$ alkyl, semi-fluorinated $C_1$-$C_4$ alkyl, and perfluorinated $C_1$-$C_4$ alkyl.

$R^{28}$ and $R^{29}$ are independently selected from hydrogen, fluoro, $C_1$-$C_{24}$ alkyl, and substituted $C_1$-$C_{24}$ alkyl, or may be taken together to form a ring, and are preferably selected from hydrogen, fluoro, $C_1$-$C_{12}$ alkyl, and substituted $C_1$-$C_{12}$ alkyl.

It will be appreciated that the fluorinated polyol precursor used to synthesize the aforementioned ester has the structure of formula (VIIA)

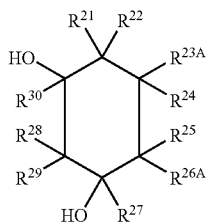
(VIIA)

wherein the R substituents are as defined for esters of formula (VII) except with respect to $R^{23A}$ and $R^{26A}$: that is, one of $R^{23A}$ and $R^{26A}$ is hydrogen and the other is hydroxyl.

In a further embodiment, a the invention provides a fluoroalkanol-substituted α,β-unsaturated ester having the structure of formula (VIII):

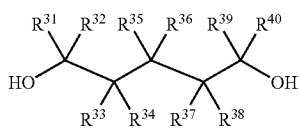
(VIII)

wherein:

$R^{31}$ and $R^{32}$ are defined as for $R^{6A}$ and $R^{7A}$, i.e., $R^{31}$ and $R^{32}$ are independently selected from hydrogen, $C_1$-$C_{24}$ alkyl, substituted $C_1$-$C_{24}$ alkyl, and —(CO)—R in which R is hydrogen, hydroxyl, halo, $C_1$-$C_{24}$ alkyl, substituted $C_1$-$C_{24}$ alkyl, amino, $C_1$-$C_{24}$ alkylamino, or di($C_1$-$C_{24}$ alkyl)amino, with the proviso that at least one of $R^{31}$ and $R^{32}$ is fluorinated, and further wherein $R^{31}$ and $R^{32}$ may be taken together to form a fluorinated alicyclic group. Preferred $R^{31}$ and $R^{32}$ moieties correspond to the preferred $R^{6A}$ and $R^{7A}$ moieties described with respect to the alkene fluoroalkanols of formula (III).

$R^{39}$ and $R^{40}$ are defined as for $R^{31}$ and $R^{32}$, respectively.

$R^{33}$, $R^{34}$, $R^{35}$, $R^{36}$, $R^{37}$, and $R^{38}$ are selected from hydrogen, $C_1$-$C_{24}$ alkyl, and substituted $C_1$-$C_{24}$ alkyl, and further wherein any two of $R^{33}$, $R^{34}$, $R^{35}$, $R^{36}$, $R^{37}$, and $R^{38}$ may be taken together to form a ring, with the proviso that one of $R^{36}$ and $R^{37}$ is hydrogen, and the other has the structure of formula (VI)

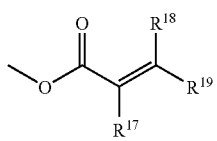
(VI)

wherein $R^{17}$, $R^{18}$, and $R^{19}$ are as defined earlier herein. Preferred $R^{33}$, $R^{34}$, $R^{35}$, and $R^{38}$ substituents are defined as for $R^4$ and $R^5$ in the fluoroalkanol-substituted α,β-unsatur-ated esters of formula (V), while preferred $R^{36}$ and $R^{37}$ substituents are defined as for $R^{15}$ and $R^{16}$ in the esters of formula (V).

Again, it will be appreciated that the fluorinated polyol precursor used to synthesize the aforementioned ester has the structure of formula (VIIIA)

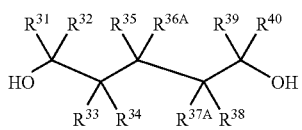
(VIIIA)

wherein the R substituents are as defined for esters of formula (VIII) except with respect to $R^{36A}$ and $R^{37A}$, one of which is hydrogen and the other of which is hydroxyl.

In a further embodiment, a fluoroalkanol-substituted α,β-unsaturated ester is provided having the structure of formula (IX)

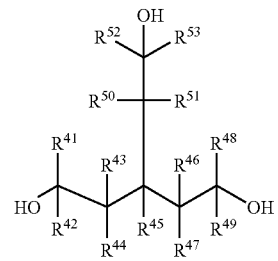
(IX)

wherein:

$R^{41}$, $R^{42}$, $R^{48}$, $R^{49}$, $R^{52}$, and $R^{53}$ are defined as for $R^{31}$, $R^{32}$, $R^{39}$, and $R^{40}$; and $R^{43}$, $R^{44}$, $R^{46}$, $R^{47}$, $R^{50}$, and $R^{51}$ are defined as for $R^{33}$, $R^{34}$, $R^{35}$, $R^{36}$, $R^{37}$, and $R^{38}$, wherein any two of $R^{43}$, $R^{44}$, $R^{46}$, $R^{47}$, $R^{50}$, and $R^{51}$ may be taken together to form an alicyclic group, with the proviso that one of $R^{45}$ and $R^{46}$ is hydrogen, and the other has the structure of formula (VI)

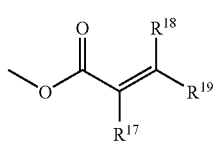
(VI)

wherein $R^{17}$, $R^{18}$, and $R^{19}$ are as defined earlier herein. Preferred $R^{43}$, $R^{44}$, $R^{46}$, $R^{47}$, $R^{50}$, and $R^{51}$ substituents are defined as for $R^4$ and $R^5$ in the fluoroalkanol-substituted α,β-unsaturated esters of formula (V), while preferred R45 and $R^{46}$ substituents are defined as for $R^{15}$ and $R^{16}$ in the esters of formula (V).

The corresponding polyol precursor has the structure of formula (IXA)

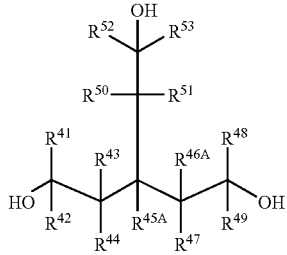
(IXA)

wherein the R substituents are as defined for esters of formula (IX) except with respect to $R^{45A}$ and $R^{46A}$, one of which is hydrogen and the other of which is hydroxyl.

Representative fluoroalkanol-substituted α,β-unsaturated esters of the invention include, but are not limited to, the following specific acrylates and methacrylates:

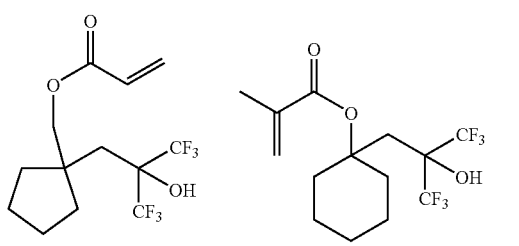

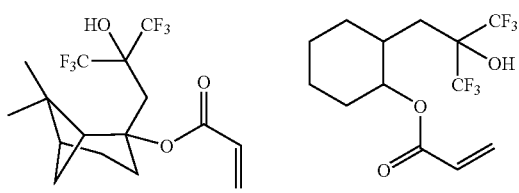

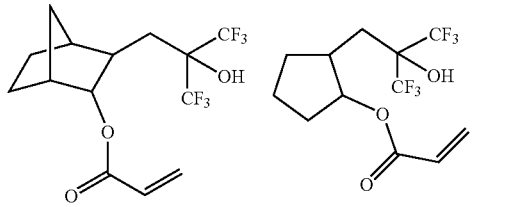

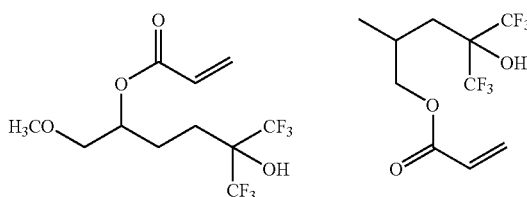

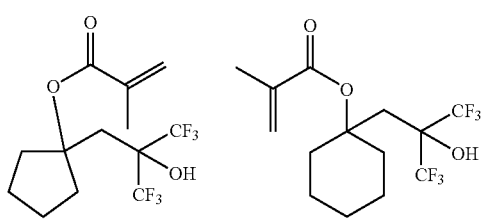

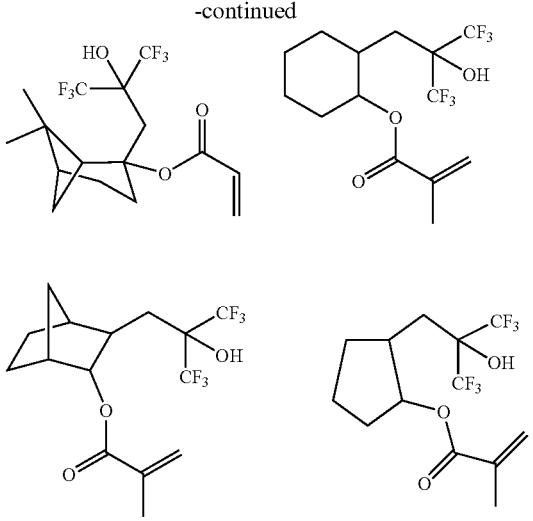

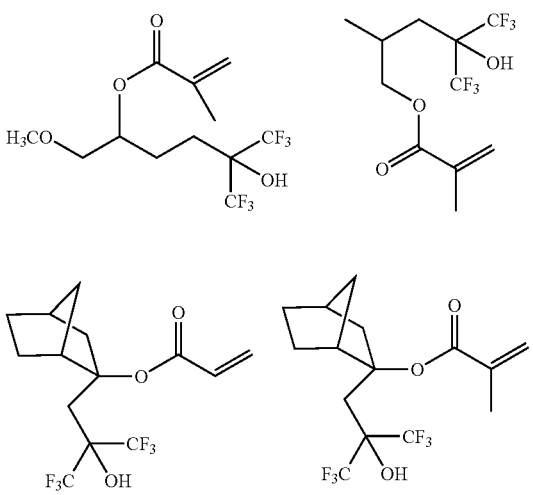

These fluoroalkanol-substituted α,β-unsaturated esters are synthesized from a fluorinated polyol as provided herein by contacting the fluorinated polyol with an acylation reagent selected from acyl chlorides of the formula Cl—(CO)—$CR^{17}$=$CR^{18}R^{19}$ and anhydrides of the formula O[(CO)—$CR^{17}$=$CR^{18}R^{19}$]$_2$, under reaction conditions effective to result in esterification of a hydroxyl group other than that present in the fluoroalkanol moiety or moieties. For instance, esterification of the fluorinated polyol of formula (V) proceeds according to Scheme 5:

Scheme 5

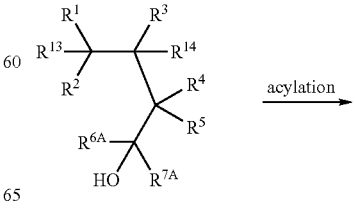

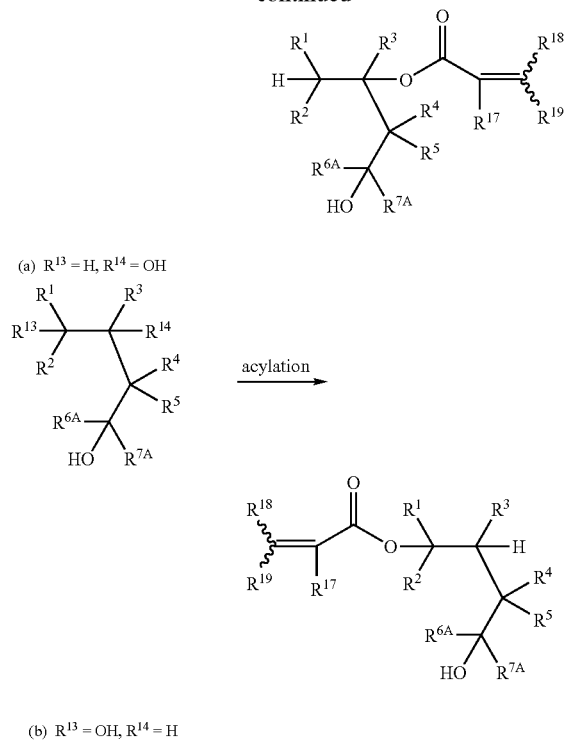

(a) $R^{13} = H, R^{14} = OH$ (b) $R^{13} = OH, R^{14} = H$

In the acylation reagents, $R^{17}$ is selected from hydrogen, fluoro, $C_1$-$C_4$ alkyl, fluorinated $C_1$-$C_4$ alkyl, —CH$_2$—COOH, —CF$_2$—COOH, —CH$_2$—COOR, and —CF$_2$—COOR$^{20}$, $R^{18}$ is hydrogen or fluoro, $R^{19}$ is hydrogen, fluoro, or —COOH, and $R^{20}$ is a nonhydrogen substituent.

In a preferred embodiment, the fluorinated polyol is treating with a deprotonating base prior to reaction with the acylation reagent.

Examples 4-8 describe acylation reactions in which fluorinated polyols are converted to fluoroalkanol-substituted α,β-unsaturated esters of the invention.

It will be appreciated that cyclic fluoroalkanol-substituted α,β-unsaturated esters such as those of formula (VII), as well as complex fluoroalkanol-substituted α,β-unsaturated esters such as those of formulae (VIII) and (IX), result from initially using a fluorinated carbonyl compound (II) in which an additional carbonyl compound is present. Such fluorinated carbonyl compounds include, without limitation, compounds of formula (II) in which $R^6$ is selected from $C_3$-$C_{25}$ acylmethyl, (fluorinated $C_2$-$C_{24}$ acyl)-substituted methyl, and (fluorinated $C_2$-$C_{24}$ acyl)-substituted difluoromethyl, particularly $C_3$-$C_{13}$ acylmethyl, (fluorinated $C_2$-$C_{12}$ acyl)-substituted methyl, and (fluorinated $C_2$-$C_{12}$ acyl)-substituted difluoromethyl, preferably $C_3$-$C_9$ acylmethyl, (fluorinated $C_2$-$C_8$ acyl)-substituted methyl, and (fluorinated $C_2$-$C_8$ acyl)-substituted difluoromethyl. Specific such compounds are those having the structure $R^{12}$—(CO)—$CR^{10}R^{11}$—(CO)—$R^7$, wherein $R^{10}$ and $R^{12}$ are H or F, $R^{12}$ is methyl or trifluoromethyl, and $R^7$ is selected from $C_1$-$C_4$ alkyl, semifluorinated $C_1$-$C_4$ alkyl, and perfluorinated $C_1$-$C_4$ alkyl. Representative such reactions are shown in Schemes 2 and 3.

The fluoroalkanol-substituted α,β-unsaturated esters can be polymerized to provide a fluoroalkanol-substituted polymer using any effective polymerization process, e.g., radical polymerization using a suitable free radical initiator such as benzoyl peroxide (BPO) or azobisisobutyronitrile (AIBN). For instance, the monomers can be dissolved in an appropriate solvent that, at reflux, will afford a medium that maintains a constant temperature suitable for activation of the initiator without inducing side reactions involving functional groups of the monomers. The solution can be prepared so as to afford a relatively high concentration of monomer, for example 30 wt %. The initiator is then added and the solution is degassed by bubbling with dry nitrogen. The reaction flask is then immersed in preheated oil bath and allowed to reflux for several hours. After cooling the solution to room temperature, the polymer is isolated by precipitation into an excess volume, for example twenty-fold, of an appropriate nonsolvent. The polymer is isolated by filtration, washed with the nonsolvent and dried to constant weight under vacuum. Polymers prepared using the fluoroalkanol-substituted α,β-unsaturated esters of the invention are useful in the manufacture of lithographic photoresist compositions.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

EXAMPLE 1

1,1,1-Trifluoro-2-trifluoromethyl-4-methyl-pent-4-en-2-ol (1): Hexafluoroacetone (238 g) and 120 g of isobutylene were condensed into a lecture bottle using Dry Ice/2-propanol cooling. The temperature was raised in the sealed vessel to 20° C. while stirring in a water bath and temperature maintained overnight. The next morning the temperature was raised to 50° C. for 2 hours. After cooling, excess isobutylene was bled off and the product distilled at 100-115° C. to afford 264 g (83%) of a clear liquid. The identity of the product was confirmed using $^1$H NMR spectroscopy and HRMS.

EXAMPLE 2

Synthesis of 1,1,1-trifluoro-2-trifluoromethyl-4-methyl-2,5-pentanediol (2): To a 3-necked, 500 mL round bottomed flask equipped with an overhead stirrer, digital thermometer and a 125 mL constant-pressure addition funnel with a nitrogen inlet was added 27 mL (0.27 mol) of borane-dimethylsulfide complex (10.0M in THF). The addition funnel was charged with a solution of 50 g (0.23 mol) of 1,1,1-trifluoro-2-trifluoromethyl-4-methyl-pent-4-en-2-ol (1) in 140 mL of anhydrous THF. The flask was cooled and the olefin was added slowly with stirring while maintaining a temperature below 15° C. The mixture was stirred at room temperature overnight after which time it was recooled and 100 mL (0.3 mol) of 3M NaOH (aq) was added carefully. The reaction mixture was reduced in volume on a rotary evaporator and subsequently co-evaporated with two 500 mL portions of diethyl ether. The resulting heavy oil was taken up in 50 mL of THF and the solution transferred to a 250 mL 3-necked round bottomed flask equipped with a 125-mL addition funnel, a digital thermometer, and a magnetic stirbar. The addition funnel was charged with 70 mL of 30% hydrogen peroxide. The flask was cooled and the hydrogen peroxide added slowly with stirring. After stirring overnight at room temperature, the solution was diluted with 500 mL of diethyl ether and adjusted to pH 6 (wet litmus)

with 5% HCl. The ether layer was separated and the aqueous layer was extracted with 2×250 mL of ether. The combined organic phases were washed with 2×500 mL of saturated ammonium chloride and brine, dried over MgSO$_4$ and evaporated to a yellow oil. The oil was purified by distillation through a Vigreux column, bp 57° C.@1.0 mm Hg to yield 46 g (85%) of (2) as a low melting solid. The identity of the product was confirmed using 1H NMR spectroscopy and HRMS.

EXAMPLE 3

1,1,1-Trifluoro-2-trifluoromethyl-2,5-pentanediol (4) and 1,1,1-trifluoro-2-trifluoromethyl-2,4-pentanediol (5): To a 3-necked, 3-L round bottomed flask equipped with an overhead stirrer, digital thermometer and a 1-L constant-pressure addition funnel with a nitrogen inlet was added 974 mL (1.95 mol) of borane-dimethylsulfide complex (2.0 M in THF). The addition funnel was charged with a solution of 353 g (1.7 mol) of 1,1,1-trifluoro-2-trifluoromethyl-pent-4-en-2-ol (3) (synthesized as in Example 1 from hexafluoroacetone and propene) in 400 mL of anhydrous THF. The flask was cooled and the olefin was added slowly with stirring while maintaining a temperature below 15° C. The mixture was stirred at room temperature for two days after which time it was recooled and 750 mL (2.25 mol) of 3 M NaOH (aq) was added carefully. The reaction mixture was reduced in volume on a rotary evaporator and subsequently co-evaporated with two 500 mL portions of diethyl ether. The resulting heavy oil was taken up in 300 mL of THF and the solution transferred to a 1-L 3-necked round-bottomed flask equipped with a 250-mL addition funnel, a digital thermometer, and a magnetic stir bar. The addition funnel was charged with 250 mL of 30% hydrogen peroxide. The flask was cooled and the hydrogen peroxide added slowly with stirring. After stirring overnight at room temperature, the solution was diluted with 1 L of diethyl ether and adjusted to pH 6 (wet litmus) with 5% HCl. The ether layer was separated and the aqueous layer was extracted with 2×500 mL of ether. The combined organic phases were washed with 2×500 mL of saturated ammonium chloride and brine, dried over MgSO$_4$ and evaporated to a crude yield of 379 g of a 45:55 (2°:1°) mixture of the two title alcohols. The diols were separated by distillation through a 12" Vigreux, bp 47° C. at 1.0 mm Hg (2° alcohol) and bp 55° C. at 1.0 mm Hg (1° alcohol). The 1° alcohol (4) is a viscous oil while the 2° alcohol (5) is a low melting solid.

EXAMPLE 4

1,1,1-Trifluoro-2-trifluoromethyl-2-hydroxy-5-pentyl methacrylate (6): To a 3-necked, 2L round-bottomed flask equipped with an overhead stirrer, digital thermometer and a 1-L constant-pressure addition funnel with a nitrogen inlet was added 590 mL (0.944 mol) of n-butyllithium (1.6 M in hexane). The addition funnel was charged with a solution of 107 g (0.47 mol) of 1,1,1-trifluoro-2-trifluoromethyl-2,5-pentanediol (4) in 300 mL of anhydrous THF. The flask was cooled and the diol was added dropwise with stirring while maintaining a temperature below 15° C. The resulting yellow-orange solution was stirred for an additional 2 hours at which time a solution of 54.5 g (0.52 mol) of methacryloyl chloride in 200 mL of anhydrous THF was added dropwise over 1 h at 10° C. The reaction mixture was allowed to reach room temperature overnight after which it was diluted with 500 mL of diethyl ether and washed with 2×500 mL of saturated ammonium chloride and brine, dried over MgSO$_4$, evaporated and distilled at 74° C. at 1.0 mm Hg (0.5 g of phenothiazine was added to the pot prior to distillation) to yield 109 g (79%) of the title compound. The identity of the product was confirmed using $^1$H NMR spectroscopy and HRMS.

EXAMPLE 5

1,1,1-Trifluoro-2-trifluoromethyl-2-hydroxy-4-pentyl methacrylate (7):
1,1,1-Trifluoro-2-trifluoromethyl-2-hydroxy-4-pentyl methacrylate was synthesized according to the method of Example 4, substituting 142 g (0.63 mol) of 1,1,1-2-trifluoromethyl-2,4-pentanediol (5) for 1,1,1-trifluoro-2-trifluoromethyl-2,5-pentanediol (4), and using 793 mL (1.27 mol) of n-butyllithium (1.6M in hexane) and 73 g (0.69 mol) of methacryloyl chloride to yield, after distillation at 67° C.@1.0 mm Hg, 142 g (76%) of the 2° methacrylate as a clear, colorless oil.

EXAMPLE 6

1,1,1-Trifluoro-2-trifluoromethyl-2-hydroxy-4-methyl-5-pentyl methacrylate (8): The title compound was prepared by method of Example 4, substituting 43 g (0.181 mol) of 1,1,1-trifluoro-2-trifluoromethyl-4-methyl-2,5-pentanediol (2) for 1,1,1-trifluoro-2-trifluoromethyl-2,5-pentanediol (4) and 226 mL (0.362 mol) of methyllithium (1.6M in ether) in lieu of the n-butyllithium, and using 20.7 g (0.199 mol) of methacryloyl chloride, to yield 35 g (76%) of the title compound as a clear colorless oil.

EXAMPLE 7

1,1,1-Trifluoro-2-trifluoromethyl-2-hydroxy-4-methyl-5-pentyl acrylate (9): 1,1,1-Trifluoro-2-trifluoromethyl-2-hydroxy-4-methyl-5-pentyl acrylate was synthesized according to the method of Example 4 but substituting (a) 60 g (0.25 mol) of 1,1,1-trifluoro-2-trifluoromethyl-4-methyl-2,5-pentanediol (2) for diol (4), (b) 311 mL (0.497 mol) of methyllithium (1.6M in ether) for the n-butyllithium, and (c) 22.3 g (0.248 mol) of acryloyl chloride for the methacryloyl chloride, to yield 58 g (86%) of the title compound as a clear colorless oil.

EXAMPLE 8

1,1,1-Trifluoro-2-hydroxy-2-trifluoromethyl-4-pentyl norbornene-5-carboxylate (11):
(a) Preparation of norbornene-5-carbonylchloride (10): A 1-L, three-neck round-bottom flask equipped with a magnetic stirrer, digital thermometer, glass stopper, an addition funnel with a nitrogen gas purge, and a dry-ice cooling bath was charged with freshly distilled cyclopentadiene (248 g, 3.75 mol), which was cooled to 0° C. The addition funnel was charged with of freshly distilled acryloyl chloride (317 g, 3.5 mol), which was added dropwise to the reaction over about three hours while maintaining the reaction temperature between 0° C. and 10° C. After the acryloyl chloride addition was complete, the cooling bath was removed and the reaction allowed to warm to room temperature overnight. The reaction mixture was distilled under vacuum, collecting 533 g of norbornene-5-carbonylchloride (10), distilling at 54-56° C. at a pressure of 300 milliTorr.
(b) 1,1,1-Trifluoro-2-hydroxy-2-trifluoromethyl-4-pentyl norbornene-5-carboxylate (11): N-butyllithium (1600 ml) (2.56 mol, 1.6M solution in hexanes) was added to a 3-L, three-necked round bottomed flask equipped with an overhead stirrer, a digital thermometer, a 500-mL capacity constant-pressure dropping funnel and a nitrogen inlet. The dropping funnel was charged with a solution of 1,1,1-trifluoro-2-trifluoromethyl-2,4-pentanediol (5) (289 g, 1.28 mol) in anhydrous THF (250 ml). The flask was cooled in ice and the THF solution was slowly added over about 2 hours, while maintaining a temperature below 10° C. Once the addition was complete, the dropping funnel was recharged with a solution of norbornene-5-carbonylchloride (201 g, 1.28 mol) in anhydrous THF (250 ml), which was then slowly added over about 1.5 hours, while maintaining a temperature below 10° C. The solution was allowed to reach room temperature with stirring overnight. The resulting suspension was transferred to a 4-L separatory funnel and washed once with water (1 L). The organic layer was separated and the aqueous wash was adjusted to pH 6 (litmus) with concentrated HCl and extracted twice with ether (1 L). The combined organic solutions were washed once with water and once with brine and dried over anhydrous magnesium sulfate. The suspension was filtered, the solvent removed on a rotary evaporator and the resulting oil distilled twice at 120° C. and 0.5 mm Hg to yield 387 g of the title compound as an oil.

EXAMPLE 9

2-(Cyclopenten-1'-yl)-1,1,1-trifluoro-2-trifluoromethyl-2-propanol (13): Hexafluoroacetone (105 g, 0.63 mol) was added to a 250 mL bomb cooled to −50° C. containing exo-methylenecyclopentane (50 g, 0.61 mol). The bomb was sealed and warmed by placing in ice water then allowed to come to room temperature. Negligible pressure increase occurred. Reaction heated to 50° C. for 1 hour, then cooled in ice bath and opened. Volatiles removed under light vacuum to give a colorless oil, 27.3 g (90.4% yield).

EXAMPLE 10

2-(6',6'-Dimethylbicyclo[3.1.1]hepten-2'-yl)-1,1,1-trifluoro-2-trifluoromethyl-2-propanol (14): Beta-pinene (50.9 g, 0.373 mol) was dissolved in chloroform (100 mL) in a 250 mL RB flask under a nitrogen blanket with a dry ice condenser. To this was added hexafluoroacetone gas (62 g, 0.37 mol), maintaining the temperature below 40° C. with a water bath. Reaction was monitored by GC, and additional hexafluoroacetone was added until complete conversion was obtained. The chloroform was removed under vacuum.

EXAMPLE 11

1,1,1,7,7,7-Hexafluoro-2,6-bis(trifluoromethyl)-4-methyl-2,6-hept-3-ene-2,6-diol (15): Hexafluoroacetone (22.6 g) and isobutene (3.4 g) were condensed into a 75 mL bomb at −50° C. The bomb was sealed and allowed to rise to room temperature, then heated to 50° C. overnight. The next day the material was dissolved into diethyl ether to remove from the bomb, and the product recovered on a rotary evaporator as a white solid (22.4 g). H-NMR, C-NMR, F-NMR, and GC/MS were used to confirm structure. The H-NMR data support an internal double bond.

EXAMPLE 12

3-(Bicyclo[2.2.1]hept-2-ene-2-yl)-1,1,1-trifluoro-2-trifluoromethyl-2-propanol: Hexafluoracetone (21.0 g) and 2-exo-methylenenorbornane were added to a bomb at −50° C., sealed, then brought to room temperature in a water bath to control the moderate exotherm. The next day the bomb was heated to 50° C. for 3 hours, then cooled. A colorless liquid (33.5 g) was recovered.

We claim:

1. A fluoroalkanol-substituted α,β-unsaturated ester having the structure of formula (V)

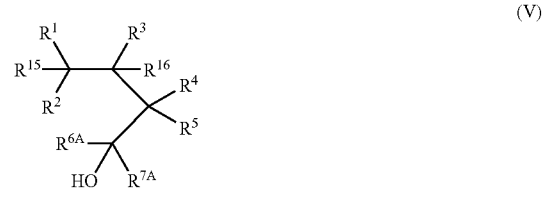

wherein:

$R^1$ is selected from hydrogen, $C_1$-$C_{24}$ alkyl, substituted $C_1$-$C_{24}$ alkyl, $C_1$-$C_{24}$ alkoxy, and substituted $C_1$-$C_{24}$ alkoxy;

$R^2$, R3, $R^4$, and $R^5$ are independently selected from hydrogen, $C_1$-$C_{24}$ alkyl, and substituted $C_1$-$C_{24}$ alkyl, and further wherein any two of $R^1$, $R^2$, $R^3$, $R^4$, and $R^5$ may be taken together to form a ring;

$R^{6A}$ is selected from hydrogen, $C_1$-$C_{24}$ alkyl, substituted $C_1$-$C_{24}$ alkyl, and —(CO)—R in which R is hydrogen, hydroxyl, halo, $C_1$-$C_{24}$ alkyl, substituted $C_1$-$C_{24}$ alkyl, amino, $C_1$-$C_{24}$ alkylamino, or di($C_1$-$C_{24}$ alkyl)amino;

$R^{7A}$ is $C_1$-$C_{24}$ alkyl or substituted $C_1$-$C_{24}$ alkyl, and further wherein $R^{6A}$ and $R^{7A}$ may be taken together to form a ring, with the proviso that at least one of $R^{6A}$ and $R^{7A}$ is fluorinated; and one of $R^{15}$ and $R^{16}$ is hydrogen, and the other has the structure of formula (VI)

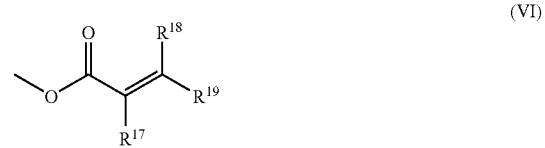

in which $R^{17}$ is selected from hydrogen, fluoro, $C_1$-$C_4$ alkyl, fluorinated $C_1$-$C_4$ alkyl, —$CH_2$—COOH, —$CF_2$—COOH, —$CH_2$—COOR$^{20}$, and —$CF_2$—COOR$^{20}$, $R^{18}$ is hydrogen or fluoro, $R^{19}$ is hydrogen, fluoro, or —COOH, and $R^{20}$ is a nonhydrogen substituent.

2. The fluoroalkanol-substituted α,β-unsaturated ester of claim 1, wherein:

$R^1$ is selected from hydrogen, $C_1$-$C_{12}$ alkyl, $C_1$-$C_2$ hydroxyalkyl, fluorinated $C_1$-$C_{12}$ alkyl, fluorinated $C_1$-$C_{12}$ hydroxyalkyl, fluorinated $C_1$-$C_{12}$ alkyl substituted with a protected hydroxyl group, and $C_1$-$C_{12}$ alkoxy;

$R^2$ is selected from hydrogen, $C_1$-$C_{12}$ alkyl and substituted $C_1$-$C_{12}$ alkyl;

$R^3$, $R^4$, and $R^5$ are independently selected from hydrogen, $C_1$-$C_{12}$ alkyl, $C_1$-$C_{12}$ hydroxyalkyl, fluorinated $C_1$-$C_{12}$ alkyl, fluorinated $C_1$-$C_{12}$ hydroxyalkyl, and fluorinated $C_1$-$C_{12}$ alkyl substituted with a protected hydroxyl group, and further wherein any two of $R^1$, $R^3$, $R^4$, and $R^5$ may be taken together to form a $C_3$-$C_{30}$ alicyclic group;

$R^{6A}$ is selected from hydrogen, $C_1$-$C_{12}$ alkyl, and $C_1$-$C_{12}$ haloalkyl;

$R^{7A}$ is $C_1$-$C_{12}$ alkyl or $C_1$-$C_{12}$ haloalkyl;

$R^{17}$ is selected from hydrogen, fluoro, methyl, trifluoromethyl, —$CH_2$—COOH, and —$CH_2$—COOR$^{20}$;

$R^{18}$ and $R^{19}$ are independently selected from hydrogen and fluoro; and $R^{20}$ is selected from $C_1$-$C_{12}$ alkyl and substituted $C_1$-$C_{12}$ alkyl.

3. The fluoroalkanol-substituted α,β-unsaturated ester of claim 2, wherein:

$R^1$ is selected from hydrogen, $C_1$-$C_8$ alkyl, $C_1$-$C_8$ alkoxy, and fluorinated hydroxyalkyl having the structure -$(L^1)_{n1}$-$CR^8R^9$—OH in which n1 is zero or 1, $L^1$ is $C_1$-$C_6$ aliphatic, $R^8$ is selected from hydrogen, $C_1$-$C_8$ alkyl, and fluorinated $C_1$-$C_8$ alkyl, and $R^9$ is fluorinated $C_1$-$C_8$ alkyl;

$R^2$ is hydrogen or $C_1$-$C_8$ alkyl;

$R^3$, $R^4$, and $R^5$ are independently selected from hydrogen, $C_1$-$C_8$ alkyl, and fluorinated hydroxyalkyl having the structure -$(L^2)_{n2}$-$CR^{8A}R^{9A}$—OH in which n2 is zero or 1, $L^2$ is $C_1$-$C_6$ aliphatic, $R^{8A}$ is selected from hydrogen, $C_1$-$C_8$ alkyl, and fluorinated $C_1$-$C_8$ alkyl, and $R^{9A}$ is fluorinated $C_1$-$C_8$ alkyl, and further wherein any two of $R^1$, $R^3$, $R^4$, and $R^5$ may be taken together to form a $C_3$-$C_{18}$ alicyclic group;

$R^{6A}$ is selected from hydrogen, $C_1$-$C_8$ alkyl, and fluorinated $C_1$-$C_8$ alkyl;

$R^{7A}$ is $C_1$-$C_8$ alkyl or fluorinated $C_1$-$C_8$ alkyl;

$R^{17}$ is selected from hydrogen and methyl; and $R^{18}$ and $R^{19}$ are hydrogen.

4. The fluoroalkanol-substituted α,β-unsaturated ester of claim 3, wherein:

$R^1$ is selected from hydrogen, $C_1$-$C_4$ alkyl, $C_1$-$C_4$ alkoxy, and -$(L^1)_{n1}$-$CR^8R^9$—OH in which n1 is zero or 1, $L^1$ is $C_1$-$C_4$ aliphatic, $R^8$ is selected from hydrogen, methyl, trifluoromethyl, difluoromethyl, and fluoromethyl, and $R^9$ is selected from methyl, trifluoromethyl, difluoromethyl, and fluoromethyl;

$R^2$ is hydrogen or $C_1$-$C_4$ alkyl;

$R^3$, $R^4$, and $R^5$ are independently selected from hydrogen, $C_1$-$C_4$ alkyl, and -$(L^2)_{n2}$-$CR^{8A}R^{9A}$—OH in which n2 is zero or 1, $L^2$ is $C_1$-$C_4$ aliphatic, $R^{8A}$ is selected from hydrogen, methyl, trifluoromethyl, difluoromethyl, and fluoromethyl, and $R^{9A}$ is selected from methyl, trifluoromethyl, difluoromethyl, and fluoromethyl, and further wherein any two of $R^1$, $R^3$, $R^4$, and $R^5$ may be taken together to form a $C_5$-$C_{14}$ alicyclic group;

$R^{6A}$ is selected from hydrogen, $C_1$-$C_4$ alkyl, semi-fluorinated $C_1$-$C_4$ alkyl, and perfluorinated $C_1$-$C_4$ alkyl; and $R^{7A}$ is selected from $C_1$-$C_4$ alkyl, semi-fluorinated $C_1$-$C_4$ alkyl, and perfluorinated $C_1$-$C_4$ alkyl.

5. The fluoroalkanol-substituted α,β-unsaturated ester of claim 3 wherein $R^2$ and $R^3$ are taken together to form a $C_3$-$C_{18}$ alicyclic group.

6. The fluoroalkanol-substituted α,β-unsaturated ester of claim 4, wherein $R^2$ and $R^3$ are taken together to form a $C_5$-$C_{14}$ alicyclic group.

7. The fluoroalkanol-substituted α,β-unsaturated ester of claim 4, wherein $R^4$ and $R^5$ are hydrogen.

8. The fluoroalkanol-substituted α,β-unsaturated ester of claim 5, wherein $R^4$ and $R^5$ are hydrogen.

9. The fluoroalkanol-substituted α,β-unsaturated ester of claim 6, wherein $R^4$ and $R^5$ are hydrogen.

10. The fluoroalkanol-substituted α,β-unsaturated ester of claim 4, wherein $R^{6A}$ and $R^{7A}$ are both trifluoromethyl.

11. The fluoroalkanol-substituted α,β-unsaturated ester of claim 4, wherein one of $R^{6A}$ and $R^{7A}$ is methyl and the other is trifluoromethyl.

12. The fluoroalkanol-substituted α,β-unsaturated ester of claim 1, wherein $R^{15}$ is hydrogen and $R^{16}$ has the structure of formula (VI)

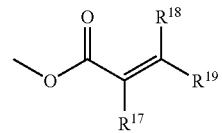

(VI)

13. The fluoroalkanol-substituted α,β-unsaturated ester of claim 1, wherein $R^{15}$ has the structure of formula (VI)

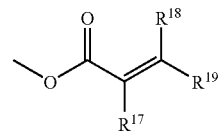

(VI)

and $R^{16}$ is hydrogen.

14. A method for synthesizing a fluoroalkanol-substituted α,β-unsaturated ester from a fluorinated polyol having the structure of formula (IV)

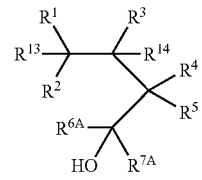

(IV)

wherein $R^1$ is selected from hydrogen, $C_1$-$C_{24}$ alkyl, substituted $C_1$-$C_{24}$ alkyl, $C_1$-$C_{24}$ alkoxy, and substituted $C_1$-$C_{24}$ alkoxy, $R^2$, $R^3$, $R^4$, and $R^5$ are independently selected from hydrogen, $C_1$-$C_{24}$ alkyl, and substituted $C_1$-$C_{24}$ alkyl, and further wherein any two of $R^1$, $R^2$, $R^3$, $R^4$, and $R^5$ may be taken together to form an alicyclic group, $R^{6A}$ is selected from hydrogen, $C_1$-$C_{24}$ alkyl, substituted $C_1$-$C_{24}$ alkyl, and —(CO)—R in which R is hydrogen, hydroxyl, halo, $C_1$-$C_{24}$ alkyl, substituted $C_1$-$C_{24}$ alkyl, amino, $C_1$-$C_{24}$ alkylamino, or di($C_1$-$C_{24}$ alkyl)amino, $R^{7A}$ is $C_1$-$C_{24}$ alkyl or substituted $C_1$-$C_{24}$ alkyl, and further wherein $R^{6A}$ and $R^{7A}$ may be taken together to form a ring, with the proviso that at least one of $R^{6A}$ and $R^{7A}$ is fluorinated, and one of $R^{13}$ and $R^{14}$ is hydroxyl and the other is selected from hydrogen and hydroxyl, the method comprising:

contacting the fluorinated polyol with an acylation reagent selected from acyl chlorides of the formula Cl—(CO)—$CR^{17}$=$CR^{18}R^{19}$ and anhydrides of the formula O[(CO)—$CR^{17}$=$CR^{18}R^{19}$]$_2$ under reaction conditions effective to result in esterification of a hydroxyl group present at $R^{13}$, $R^{14}$, or at both $R^{13}$ and $R^{14}$, to provide an —O—(CO)—$CR^{17}$=$CR^{18}R^{19}$ substituent, wherein $R^{17}$ is selected from hydrogen, fluoro, $C_1$-$C_4$ alkyl, fluorinated $C_1$-$C_4$ alkyl, —$CH_2$—COOH, —$CF_2$—COOH, —$CH_2$—$COOR^{20}$, and —$CF_2$-$COOR^{20}$, $R^{18}$ is hydrogen or fluoro, $R^{19}$ is hydrogen, fluoro, or —COOH, and $R^{20}$ is a nonhydrogen substituent.

15. The method of claim 14, wherein prior to admixture of the fluorinated polyol with the acylation reagent, the fluorinated polyol is treated with a deprotonating base.

16. The method of claim 15, wherein:
   $R^1$ is selected from hydrogen, $C_1$-$C_4$ alkyl, $C_1$-$C_4$ alkoxy, and $-(L^1)_{n1}-CR^8R^9-OH$ in which n1 is zero or 1, $L^1$ is $C_1$-$C_4$ aliphatic, $R^8$ is selected from hydrogen, methyl, trifluoromethyl, difluoromethyl, and fluoromethyl, and $R^9$ is selected from methyl, trifluoromethyl, difluoromethyl, and fluoromethyl;
   $R^2$ is hydrogen or $C_1$-$C_4$ alkyl;
   $R^3$, $R^4$, and $R^5$ are independently selected from hydrogen, $C_1$-$C_4$ alkyl, and $-(L^2)_{n2}-CR^{8A}R^{9A}-OH$ in which n2 is zero or 1, $L^2$ is $C_1$-$C_4$ aliphatic, $R^{8A}$ is selected from hydrogen, methyl, trifluoromethyl, difluoromethyl, and fluoromethyl, and $R^{9A}$ is selected from methyl, trifluoromethyl, difluoromethyl, and fluoromethyl, and further wherein any two of $R^1$, $R^3$, $R^4$, and $R^5$ may be taken together to form a $C_5$-$C_{12}$ alicyclic group;
   $R^{6A}$ is selected from hydrogen, $C_1$-$C_4$ alkyl, semi-fluorinated $C_1$-$C_4$ alkyl, and perfluorinated $C_1$-$C_4$ alkyl; and
   $R^{7A}$ is selected from $C_1$-$C_4$ alkyl, semi-fluorinated $C_1$-$C_4$ alkyl, and perfluorinated $C_1$-$C_4$ alkyl.

17. The method of claim 15, wherein the acylation reagent is an acyl chloride of the formula $Cl-(CO)-CR^{17}=CR^{18}R^{19}$.

18. The method of claim 17, wherein $R^{17}$ is selected from hydrogen, fluoro, methyl, trifluoromethyl, $-CH_2-COOH$, and $-CH_2-COOR^{20}$, $R^{18}$ and $R^{19}$ are independently selected from hydrogen and fluoro, and $R^{20}$ is selected from $C_1$-$C_{12}$ alkyl and substituted $C_1$-$C_{12}$ alkyl.

19. The method of claim 15, wherein the acylation reagent is an anhydride of the formula $O[(CO)-CR^{17}=CR^{18}R^{19}]_2$.

20. The method of claim 19, wherein $R^{17}$ is selected from hydrogen, fluoro, methyl, trifluoromethyl, $-CH_2-COOH$, and $-CH_2-COOR^{20}$, $R^{18}$ and $R^{19}$ are independently selected from hydrogen and fluoro, and $R^{20}$ is selected from $C_1$-$C_{12}$ alkyl and substituted $C_1$-$C_{12}$ alkyl.

21. A fluoroalkanol-substituted α,β-unsaturated esters selected from the group consisting of

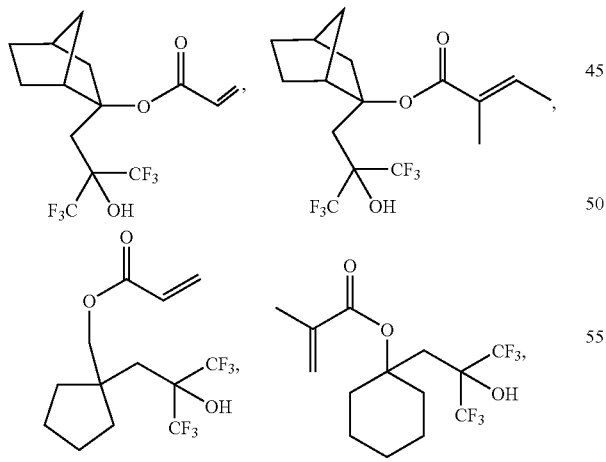

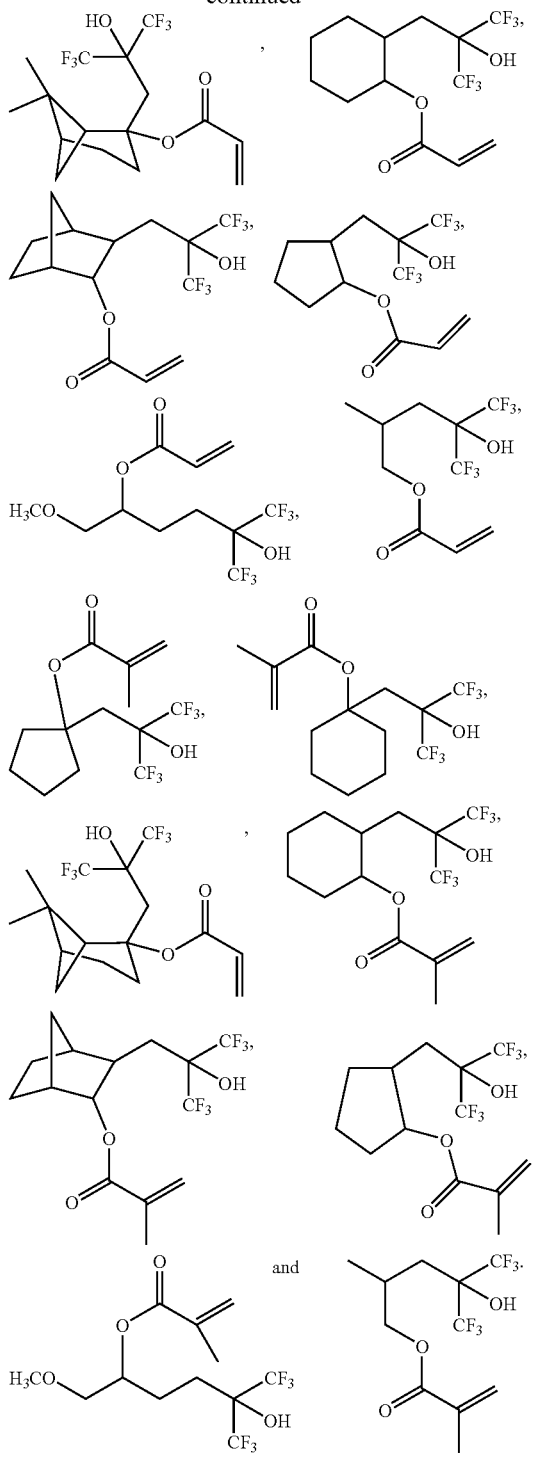

* * * * *